| United States Patent [19] | [11] 3,983,153 |
| Schneider | [45] Sept. 28, 1976 |

[54] RACEMIC FLUORO-SUBSTITUTED PGE$_2$ ANALOGS

[75] Inventor: William P. Schneider, Kalamazoo, Mich.

[73] Assignee: The Upjohn Company, Kalamazoo, Mich.

[22] Filed: Dec. 6, 1974

[21] Appl. No.: 530,430

Related U.S. Application Data

[63] Continuation-in-part of Ser. No. 807,405, March 14, 1969, abandoned.

[52] U.S. Cl. .................. 260/468 D; 260/247.2 R; 260/268 R; 260/293.65; 260/326.2; 260/424.9; 260/439 R; 260/448 R; 260/501.1; 260/501.15; 260/501.17; 260/501.2; 260/514 D

[51] Int. Cl.$^2$ ...................... C07C 177/00

[58] Field of Search .................. 260/468 D, 514 D

[56] References Cited
UNITED STATES PATENTS
3,514,383  5/1970  Beal et al. .................. 204/158

FOREIGN PATENTS OR APPLICATIONS
747,348  9/1970  Belgium .................. 260/468

*Primary Examiner*—Robert Gerstl

[57] ABSTRACT

This invention is racemic PGE$_2$, racemic PGF$_{2\alpha}$, racemic PGF$_{2\beta}$, racemic PGA$_2$, racemic PGB$_2$, analogs of those, and processes for making them. These compounds are useful for a variety of pharmacological purposes, including anti-ulcer, inhibition of platelet aggregation, increase of nasal patency, abortion, and wound healing.

17 Claims, No Drawings

RACEMIC FLUORO-SUBSTITUTED PGE₂ ANALOGS

CROSS REFERENCE TO RELATED APPLICATION

This application is a continuation-in-part of copending application Ser. No. 807,405, filed Mar. 14, 1969, now abandoned.

This invention relates to compositions of matter, and to methods and intermediates for producing them. In particular, the several aspects of this invention relate to racemic prostaglandin $E_2$ (PGE$_2$), racemic prostaglandin $F_2$ (PGF$_{2\alpha}$ and PGF$_{2\beta}$), racemic prostaglandin $A_2$ (PGA$_2$), racemic prostaglandin $B_2$ (PGB$_2$), to the corrsponding acetylenic prostaglandins, 5,6-dehydro-PGE$_2$, 5,6-dehydro-PGF$_{2\alpha}$, 5,6-dehydro-PGF$_{2\beta}$, 5,6-dehydro-PGA$_2$, and 5,6-dehydro-PGB$_2$; to analogs of those prostaglandins and 5,6-dehydro-prostaglandins; to processes for producing racemic PGE$_2$, PGF$_{2\alpha}$, PGF$_{2\beta}$, PGA$_2$, PGB$_2$, the corresponding 5,6-dehydro-prostaglandins, and the analogs thereof; and to chemical intermediates useful in those methods.

Optically active PGE$_2$, PGF$_{2\alpha}$, PGF$_{2\beta}$, PGA$_2$, and PGB$_2$ are known substances. All of those except PGF$_2$ have been obtained in very small quantities from certain mammalian tissues, for example, sheep vesicular glands, swine lung, and human seminal plasma. See, for example, Bergstrom et al., Pharmacol. Rev. 20, 1 (1968), and references cited therein. Optically active PGE$_2$ and PGF$_{2\alpha}$ have also been obtained in small amounts by enzymatic cyclization of arachidonic acid, for example, with certain of the enzymes of sheep vesicular glands. See, for example, U.S. Pat. No. 3,296,091. Similar enzymatic cyclizations of other unsaturated long-chain acids have been used to produce a limited group of optically active PGE$_2$ analogs See, for example, Struijk et al., Rec. Trav. Chim. 85, 1233 (1966) and Beerthuis et al., Rec. Trav. Chim. 87, 461 (1968). Optically active PGA$_2$ and PGB$_2$ have been obtained by dehydration of PGE$_2$, and optically active PGF$_{2\alpha}$ and PGF$_{2\beta}$ have been obtained by carbonyl reduction of PGE$_2$. In each case, the PGE$_2$ used was necessarily obtained as described above. See, for example, Bergstrom et al., Arkiv Kemi, 19, 563 (1963) and Pike et al., Proc. Nobel Symposium II, Stockholm (1966); Interscience Publishers, New York, p. 161 (1967).

The above-mentioned methods for producing prostaglandins are costly and difficult, the necessary biological materials are limited, and the methods are not adaptable to production of a wide variety of prostaglandin intermediates.

It is the purpose of this invention to provide processes for the production of compounds with prostaglandin-like activity in substantial amounts and at reasonable cost. The useful compounds produced according to the processes of this invention comprise racemic PGE$_2$, racemic PGF$_{2\alpha}$, racemic PGF$_{2\beta}$, racemic PGA$_2$, racemic PGB$_2$, the corresponding 5,6-dehydro-prostaglandins, and other hitherto unavailable racemic and optically active analogs thereof.

PGE$_2$ has the following structure:

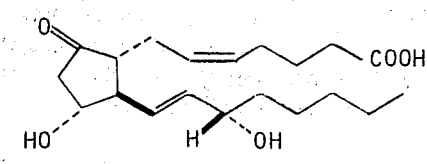

PGF$_{2\alpha}$ has the following structure:

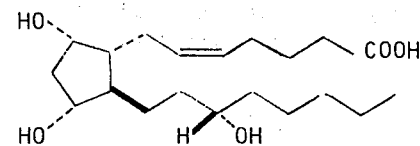

PGF$_{2\beta}$ has the following structure:

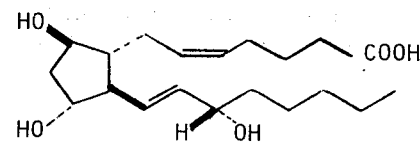

PGA$_2$ has the following structure:

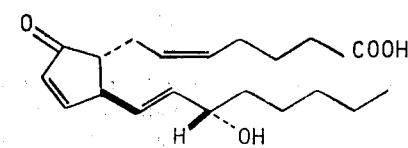

PGB$_2$ has the following structure:

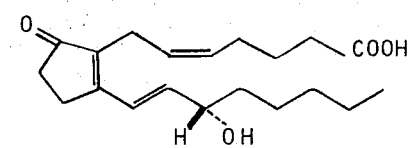

Racemic PGE$_2$, PGF$_{2\alpha}$, PGB$_{2\beta}$, PGA$_2$, and PGB$_2$ are each represented by the combination of one of the above formulas and the mirror image of that formula. See Nature, 212, 38 (1966) for discussion of the stereochemistry of the prostaglandins.

In formulas I, II, III, IV, and V, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

PGE$_2$, PGF$_{2\alpha}$, PGF$_{2\beta}$, PGA$_2$, and PGB$_2$ are derivatives of prostanoic acid which has the following structure and atom numbering:

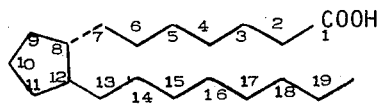

A systematic name for prostanoic acid is 7-[(2β-octyl)-cyclopent-1α-yl]heptanoic acid.

Compounds similar to formula VI but with carboxyl-terminated side chains attached to the cyclopentane ring in beta configuration are designated 8-iso-prostanoic acids, and have the following formula:

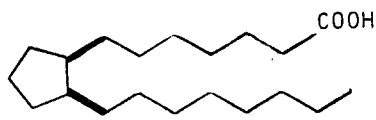

VII

A systematic name for iso-prostanoic acid is 7-[(2β-octyl)cyclopent-1β-yl]heptanoic acid.

Racemic prostaglandin E₂ and its analogs produced according to the processes of this invention are represented by the formula:

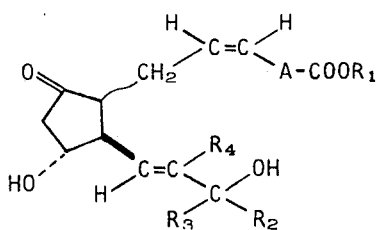

VIII wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the β-position with 3 chloro, 2 or 3 bromo, or 1, 2, or 3 iodo; wherein $R_2$ is hydrogen or alkyl of one to 10 carbon atoms, inclusive, substituted with zero to 3 fluoro; wherein $R_3$ and $R_4$ are hydrogen or alkyl of one to 4 carbon atoms, inclusive; wherein A is alkylene of one to 10 carbon atoms, inclusive, substituted with zero to 2 fluoro, and with one to 5 carbon atoms, inclusive, between

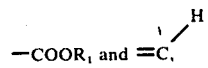

and wherein ~ indicates attachment of the

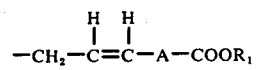

moiety to the ring in alpha or beta configuration; and pharmacologically acceptable salts thereof when $R_1$ is hydrogen.

Racemic prostaglandin F₂ and its analogs produced according to the processes of this invention are represented by the formula:

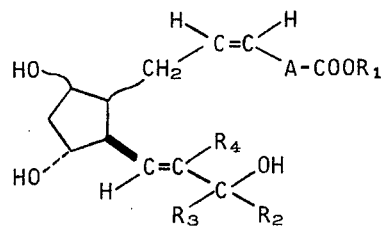

IX wherein $R_1$, $R_2$, $R_3$, $R_4$, and A are as defined above for formula VIII, and ~ indicates attachment of the hydroxy and

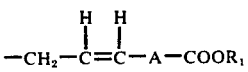

moieties to the ring in alpha or beta configuration, and pharmacologically acceptable salts thereof when $R_1$ is hydrogen. Included in formula IX are compounds wherein the configuration of the hydroxy and

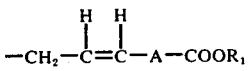

moieties are, respectively, $\alpha,\alpha$, $\alpha,\beta$, $\beta,\alpha$, and $\beta,\beta$.

Racemic prostaglandin A₂ and its analogs produced according to the processes of this invention are represented by the formulas:

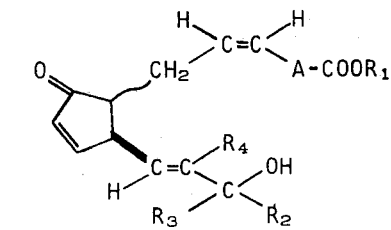

X wherein $R_1$, $R_2$, $R_3$, $R_4$, and A are as defined above for formula VIII, and ~ indicates attachment of the

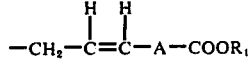

moiety to the ring in alpha or beta configuration, and pharmacologically acceptable salts thereof when $R_1$ is hydrogen.

Racemic prostaglandin B₂ and its analogs produced according to the processes of this invention are represented by the formula:

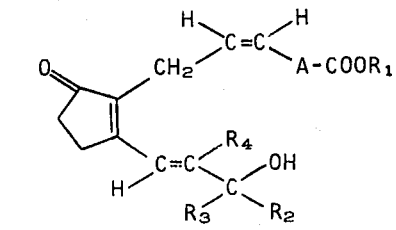

XI wherein $R_1$, $R_2$, $R_3$, $R_4$, and A are defined above for formula VIII, and pharmacologically acceptable salts thereof wherein $R_1$ is hydrogen.

The acetylenic prostaglandin, 5,6-dehydro-PGE₂, and its analogs produced according to the processes of this invention are represented by the formula:

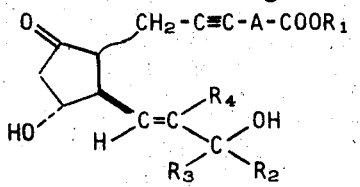

XII wherein $R_1$, $R_2$, $R_3$, $R_4$, and A are as defined above for formula VIII, and ~ indicates attachment of the —$CH_2$—C≡C—A—$COOR_1$ moiety to the ring in alpha or beta configuration, and pharmacologically acceptable salts thereof when $R_1$ is hydrogen.

The acetylenic prostaglandin, 5,6-dehydro-$PGF_2$, and its analogs produced according to the processes of this invention are represented by the formula:

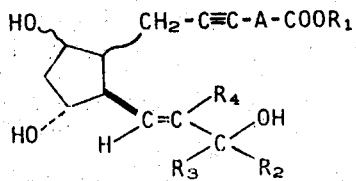

XIII wherein $R_1$, $R_2$, $R_3$, $R_4$, and A are as defined above for formula VIII, and ~ indicates attachment of the hydroxy and —$CH_2$—C≡C—A—$COOR_1$ moieties to the ring in alpha or beta configuration, and pharmacologically acceptable salts thereof when $R_1$ is hydrogen. Included in formula XIII are compounds wherein the configuration of the hydroxy and —$CH_2$—C≡C—A—$COOR_1$ moieties are, respectively $\alpha,\alpha$, $\alpha,\beta$, $\beta,\alpha$, and $\beta,\beta$.

The acetylenic prostaglandin, 5,6-dehydro-$PGA_2$, and its analogs produced according to the processes of this invention are represented by the formula:

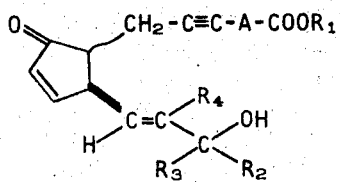

XIV wherein $R_1$, $R_2$, $R_3$, $R_4$, and A are as defined above for formula VIII, and ~ indicates attachment of the —$CH_2$—C≡C—A—$COOR_1$ moiety to the ring in alpha or beta configuration, and pharmacologically acceptable salts thereof when $R_1$ is hydrogen.

The acetylenic prostaglandin, 5,6-dehydro-$PGB_2$, and its analogs produced according to the processes of this invention are represented by the formula:

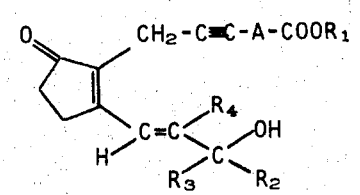

XV wherein $R_1$, $R_2$, $R_3$, $R_4$, and A are as defined above for formula VIII, and pharmacologically acceptable salts thereof when $R_1$ is hydrogen.

Formulas VIII, IX, X, XI, XII, XIII, XIV, and XV represent $PGE_2$, $PGF_2$, $PGA_2$, $PGB_2$, 5,6-dehydro-$PGE_2$, 5,6-dehydro-$PGF_2$, 5,6-dehydro-$PGA_2$, and 5,6-dehydro-$PGB_2$, respectively, when in these formulas $R_1$, $R_3$, and $R_4$ are each hydrogen $R_2$ is pentyl, A is trimethylene, the attachment of —$CH_2$—CH=λ CH—A—$COOR_1$ or —$CH_2$—C ≡ C—A—$COOR_1$ to the cyclopentane ring is in alpha configuration, and the configuration of the side chain hydroxy is S.

With regard to formulas VIII to XV, inclusive, examples of alkyl of one to 4 carbon atoms, inclusive, are methyl, ethyl, propyl, butyl, and isomeric forms thereof. Examples of alkyl of one to 8 carbon atoms, inclusive, are those given above, and pentyl, hexyl, heptyl, octyl, an isomeric forms thereof. Examples of alkyl of one to 10 carbon atoms, inclusive, are those given above, and nonyl, decyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkylene of one to 10 carbon atoms, inclusive, are methylene, ethylene, trimethylene, tetramethylene, pentamethylene, hexamethylene, heptamethylene, octamethylene, nonamethylene, and decamethylene, and isomeric branched chain forms thereof.

Examples of alkyl of one to 10 carbon atoms, inclusive, substituted with one to 3 fluoro, are 2-fluoroethyl, 2-fluorobutyl, 3-fluorobutyl, 4-fluorobutyl, 5-fluoropentyl, 4-fluoro-4-methylpentyl, 3-fluoroisoheptyl, 8fluorooctyl, 3,4-difluorobutyl, 4,4-difluoropentyl, 5,5-difluoropentyl, 5,5,5-trifluoropentyl, and 10,10,10-trifluorodecyl.

Examples of alkylene of one to 10 carbon atoms, inclusive, substituted with one or 2 fluoro, have the formulas —$CH_2CHF$—, —$CH_2CF_2$—, —$CH_2CH_2CHFCH_2$—, —$CH_2CH_2CH_2CF_2$—,

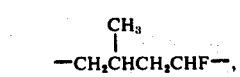
—$CH_2CHCH_2CHF$—,

—$CH_2CH_2CH_2CHFCHF$—,
—$CH_2CH_2CH_2CH_2CH_2CHF$—,
—$CH_2CH_2CH_2CH_2CH_2CF_2$—,
—$CH_2CH_2CH_2CF_2CH_2CH_2CH_2$—, and
—$CH_2CH_2CH_2CH_2CH_2CH_2CH_2CF_2$—.

$PGE_2$, $PGF_{2\alpha}$, $PGF_{2\beta}$, $PGA_2$, and $PGB_2$, and their esters and pharmacologically acceptable salts, are extremely potent in causing various biological reponses. For that reason, these compounds are useful for pharmacological purposes. See, for example, Bergstrom et al., Pharmacol, Rev. 20, 1 (1968), and references cited therein. A few of those biological responses are systemic arterial blood pressure lowering in the case of $PGE_2$, $PGF_{2\beta}$, and $PGA_2$ as measured, for example, in anesthetized (pentobarbital sodium) pentolinium-treated rats with indwelling aortic and right heart cannulas; pressor activity, similarly measured, for $PGF_{2\alpha}$; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of $PGE_2$ and $PGA_2$ as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of $PGE_2$ and $PGB_2$, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially $PGE_2$, are useful in mammals, including man, as nasal decongestants. For this purpose, the compounds are used in a dose range of about 10 µg. to about 10 mg. per ml. of a pharmacologically suitable liquid vehicle or as an aerosol spray, both for topical application.

$PGE_2$ and $PGA_2$ are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in a infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

$PGE_2$, $PGA_2$, $PGF_{2\alpha}$, and $PGF_{2\beta}$ are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.004 to about 20 mg. per kg. of body weight per day are used, the exact dose depending on the age, weight, and condition of the patient or animal, and on the frequency and route of administration.

$PGE_2$, $PGA_2$, $PGF_{2\alpha}$, and $PGF_{2\beta}$ are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

$PGE_2$ is extremely potent in causing stimulation of smooth muscle, and is also highly active in potentiating other known smooth muscle stimulators, for example, oxytocic agents, e.g., oxytocin, and the various ergot alkaloids including derivatives and analogs thereof. Therefore $PGE_2$ is useful in place of or in combination with less than usual amounts of these known smooth muscle stimulators, for example, to relieve the symptoms of paralytic ileus, to control or prevent atonic uterine bleeding after abortion or delivery, to aid in expulsion of the placenta, and during the puerperium. For these purposes, $PGE_2$ is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

$PGE_2$, $PGA_2$, and $PGF_{2\beta}$ are useful as hypotensive agents to reduce blood pressure in mammals, including man. For this purpose, the compounds are administered by intravenous infusion at the rate about 0.01 to about 50 µg. per kg. of body weight per minute or in single or multiple doses of about 25 to 500 µg. per kg. of body weight total per day.

$PGF_{2\alpha}$, $PGF_{2\beta}$, and $PGE_2$ are useful for controlling the reproductive cycle in ovulating female mammals, including humans and animals such as monkeys, rats, rabbits, dogs, cattle, and the like. For that purpose, $PGF_{2\alpha}$ is administered systemically at a dose level in the range 0.01 mg. to about 20 mg. per kg. of body weight of the female mammal, advantageously during a span of time starting approximately at the time of ovulation and ending approximately at the time of menses or just prior to menses.

As mentioned above, $PGE_2$ is a potent antagonist of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

$PGE_2$ and $PGB_2$ promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu g./ml.$ of $PGB_2$ or several times that concentration of $PGE_2$. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

Racemic $PGE_2$, racemic $PGF_2$, racemic $PGF_{2\beta}$, racemic $PGA_2$, and racemic $PGB_2$ each are useful for the purposes described above for the optically active compounds, but these racemic compounds offer the enormous advantage of being available in unlimited quantities at much lower cost. Moreover, these racemic compounds are easier to purify since they are produced by chemical reactions rather than by extraction from biological materials or enzymatic reaction mixtures.

The other racemic compounds encompassed by formulas VIII, IX, X, and XI, and also the acetylenic compounds 5,6-dehydro-$PGE_2$, 5,6-dehydro-$PGF_{2\alpha}$, 5,6-dehydro-$PGF_{2\beta}$, 5,6-dehydro-$PGA_2$, and 5,6-dehydro-$PGB_2$ and the other compounds encompassed by formulas XII, XIII, XIV, and XV each cause the biological responses described above for the corresponding known prostaglandins, and each of these novel racemic compounds is accordingly useful for the above-described corresponding purposes, and is used for those purposes in the same manner as described above.

The known optically active prostaglandins $PGE_2$, $PGF_{2\alpha}$, $PGF_{2\beta}$, $PGa_2$, and $PGB_2$ are all potent in causing multiple biological responses even at low doses. For example, $PGE_2$ is extremely potent in causing vaso-depression and smooth muscle stimulation, and also is potent as an antilipolytic agent. In striking contrast, the analogs of formulas VIII, IX, X, and XI, and also the acetylenic formula XII, XIII, XIV, and XV are substantially more specific with regard to potency in causing prostaglandin-like biological responses. Therefore, each of these novel prostaglandin analogs is surprisingly and unexpectedly more useful than one of the corresponding above-mentioned prostaglandins for at least one of the pharmacological purposes indicated above for the latter. Use of the novel analog for that purpose results in smaller undesired side effects than when the known prostaglandin is used for the same purpose.

To obtain the optimum combination of biological response specificity and potency, certain compounds within the scope of formulas VIII and IX are preferred. As discussed above, those formulas represent the $PGE_2$-type compounds and the $PGF_{2\alpha}$-type compounds, respectively. Referring to formulas VIII and IX, when $-CH_2-CH=CH-A-COOR_1$ is attached in alpha configuration and, in the case of formula IX, when the ring hydroxy is also attached in alpha configuration, stereochmistry typical of the known optically active $PGE_2$ and $PGF_{2\alpha}$, it is preferred that terminal alkyl group $R_2$ not be pentyl at the same time that alkylene group A is straight chain and unsubstituted. In other words, according to this invention, preferred formula VIII and IX compounds wherein $-CH_2-CH=CH-A-COOR_1$ and ring hydroxy are alpha are those wherein $R_2$ is branched chain or fluoro-substituted alkyl when A is straight chain unsubstituted alkylene, those wherein A is branched chain or fluoro-substituted when $R_2$ is pentyl, and those wherein $R_2$ is alkyl other than pentyl, i.e., alkyl of one to 4 carbon atoms, inclusive, or alkyl of 6 to 8 carbon atoms, inclusive. These preferred compounds exhibit superior biological response specificity and/or potency. For reasons not completely understood, fluoro-substitution or branching of at least one of A and $R_2$ in these particular groups of formula VIII and formula IX compounds, increases biological response specificity and/or potency. This is especially true in the case of A when $R_2$ is pentyl.

Certain compounds within the scope of formulas VIII to XV are especially useful for one or more of the purposes stated above for $PGE_2$, $PGF_{2\alpha}$, $PGF_{2\beta}$, $PGA_2$, and $PGB_2$, because they have a substantially longer duration of activity than other compounds within the generic formulas, including $PGE_2$, $PGF_{2\alpha}$, $PGF_{2\beta}$, $PGA_2$, and $PGB_2$, and because they can be administered orally, sublingually, intravaginally, buccally, or rectally, rather than by the usual intravenous, intramuscular, or subcutaneous injection or infusion as indicated above for the uses of these known prostaglandins and the other compounds encompassed by formulas VIII to XV. These qualities are advantageous because they facilitate maintaining uniform levels of these compounds in the body with fewer, shorter, or smaller doses, and make possible self-administration by the patient.

With reference to formulas VIII to XV, these special compounds include those wherein A is $-(CH_2)_b-Z-$, wherein b is zero, one, 2, or 3, and Z is ethylene substituted by one or 2 fluoro, methyl, or ethyl, or by one alkyl of 3 or 4 carbon atoms. These special compounds also include those wherein $R_2$ is $-(CH_2)_d-X$, wherein d is zero, one, 2, 3, or 4, and X is isobutyl, tert-butyl, 3,3-difluorobutyl, 4,4-difluorobutyl, or 4,4,4-trifluorobutyl. These special compounds also include those wherein A is $-(CH_2)_b-Z-$ as above defined, and $R_2$ is $-(CH_2)_d-X$ as above defined. Especially preferred among these special compounds are those wherein $R_3$ and $R_4$ are both hydrogen.

In the case of Z, the divalent ethylene group, $-CH_2-CH_2-$, is substituted on either or both carbon atoms, i.e., alpha and/or beta to the carboxylate function. For example, Z is $-CH_2-CHF-$, $-CHF-CH_2-$, $-CH_2-CF_2-$, $-CF_2-CH_2-$, $-CHF-CHF-$, $-CH_2-CH(CH_3)-$, $-CH(CH_3)-CH_2-$, $-CH_2-C(CH_3)_2-$, $-C(CH_3)_2-CH_2-$, $-CH(CH_3)-CH(CH_3)-$, and similarly for ethyl, and for one fluoro and one methyl, one fluoro and one ethyl, and one methyl and one ethyl. Z is alternatively ethylene substituted on either carbon atom with propyl, isopropyl, butyl, isobutyl, sec-butyl, or tert-butyl.

Although all of the special compounds just described have the special advantages of long duration and oral, sublingual intravaginal, and rectal routes of administration, there is a still more limited group of compounds encompassed by these formulas which have these qualities in a particularly high degree. Those are the compounds wherein A is $-CH_2-Z-$, i.e., wherein b in $-(CH_2)_b-Z-$ is one, especially when Z is ethylene with one fluoro or methyl, with 2 fluoro or 2 methyl on the same carbon atom, or with butyl, isobutyl, sec-butyl, or tert-butyl on the carbon atoms alpha (adjacent) to the carboxylate function, the compounds wherein $R_2$ is $-CH_2CH_2CH_2C(CH_3)_3$, $-CH_2CH_2CH_2CH(CH_3)_2$, $-CH_2CH_2CH_2CH_2CF_3$, $-CH_2CH_2CH_2CH_2CHF_2$, or $-CH_2CH_2CH_2CF_2CH_3$, and the compounds wherein both A and $R_2$ are both defined in these more limited ways.

Racemic $PGE_2$, racemic $PGF_{2\alpha}$, racemic $PGF_{2\beta}$, racemic $PGA_2$, racemic $PGB_2$, the corresponding 5,6-dehydro, and the other compounds encompassed by formulas VIII to XV, including the special classes of compounds described above are used for the purposes described above in the free acid form, in ester form, or in pharmacologically acceptable salt form. When the ester form is used, the ester is any of those within the above definition of $R_1$. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these formula VIII to XV compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of formulas VIII to XV are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isontonic solutions are preferred. For that purpose, it is preferred because of increased water solubility that $R_1$ in the formula VIII to XV compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

Racemic $PGE_2$, racemic $PGF_{2\alpha}$, racemic $PGF_{2\beta}$, racemic $PGA_2$, racemic $PGB_2$, the corresponding 5,6-dehydroprostaglandins, and the other compounds encompassed by formulas VIII to XV are produced by the reactions and procedures described hereinafter.

Racemic $PGF_{2\alpha}$, racemic $PGF_{2\beta}$, 5,6-dehydro-$PGF_{2\alpha}$, 5,6-dehydro-$PGF_{2\beta}$, and the other $PGF_2$-type compounds encompassed by formulas IX and XIII are prepared by carbonyl reduction of the corresponding $PGE_2$-type compounds encompassed by formulas VIII and XII. For example, carbonyl reduction of racemic $PGE_2$ gives a mixture of racemic $PGF_{2\alpha}$ and racemic $PGF_{2\beta}$.

These ring carbonyl reductions are carried out by methods known in the art for ring carbonyl reductions of known prostanoic acid derivatives. See, for example, Bergstrom et al., Arkiv Kemi, 19, 563 (1963), and Acta Chem. Scand. 16, 969 (1962), and British Pat. Specification No. 1,097,533. Any reducing agent is used which does not react with carbon-carbon double bonds or ester groups. Preferred reagents are aluminum (tri-tert-butoxy) hydride and the metal borohydrides, especially sodium, potassium and zinc borohydrides. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research, 5, 117 (1964). Especially preferred as separation methods are partition chromatographic procedures, both normal and reversed phase, preparative thin layer chromatography, and countercurrent distribution procedures.

Racemic $PGA_2$, 5,6-dehydro-$PGA_2$, and the other $PGA_2$-type compounds encompassed by formulas X and XIV are prepared by acidic dehydration of the corresponding $PGE_2$-type compounds encompassed by formulas VIII and XII. For example, acidic dehydration of racemic $PGE_2$ gives racemic $PGA_2$.

These acidic dehydrations are carried out by methods known in the art for acidic dehydrations of known prostanoic acid derivatives. See, for example, Pike et al., Proc. Nobel Symposium II, Stockholm (1966); Interscience Publishing Co., New York, pp. 162-163 (1967), and British Pat. Specification 1,097,533. Alkanoic acids of 2 to 6 carbon atoms, inclusive, especially acetic acid, are preferred acids for this acidic dehydration.

Racemic $PGB_2$, 5,6-dehydro-$PGB_2$, and the other compounds encompassed by formulas XI and XV are prepared by basic dehydration of the corresponding $PGE_2$-type compounds encompassed by formulas VIII and XII, or by contacting the corresponding $PGA_2$-type compounds encompassed by formulas X and XIV with base. For example, both racemic $PGE_2$ and racemic $PGA_2$ give racemic $PGB_2$ on treatment with base. Presumably the base first causes dehydration of the $PGE_2$ to $PGA_2$, and then causes the ring double bond of $PGA_2$ to migrate to a new position.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The $PGE_2$-type or $PGA_2$-type compound is maintained in such a reaction medium until no further $PGB_2$-type compound is formed, as shown by the characteristic ultraviolet light absorption near 278 m$\mu$ for the $PGB_2$-type compound.

These various transformations of the $PGE_2$-type compounds of formulas VIII and XII to the $PGF_2$-type, $PGA_2$-type, and $PGB_2$-type compounds are shown in Chart A, wherein $R_1$, $R_2$, $R_3$, $R_4$, A, and $\sim$ are as defined above, and V is cis—CH=CH— or —C≡C-.

Racemic $PGE_2$, 5,6-dehydro-$PGE_2$, and the other $PGE_2$-type compounds encompassed by formulas VIII and XII are prepared by the multi-step processes outlined in Charts B, C, D, E, and F.

CHART A

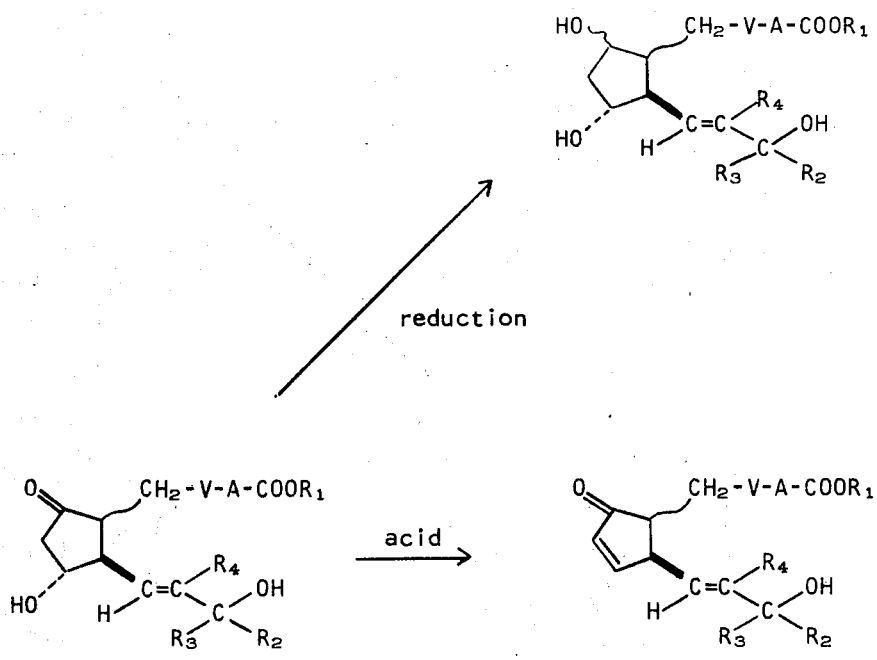

CHART A -continued
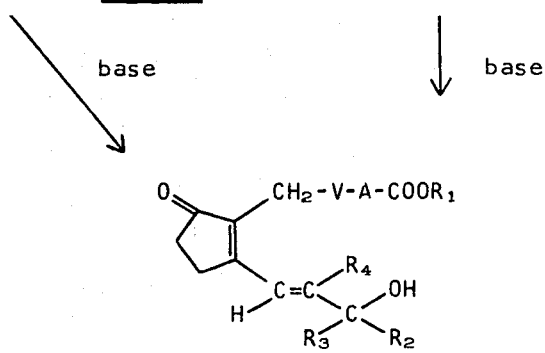
CHART B
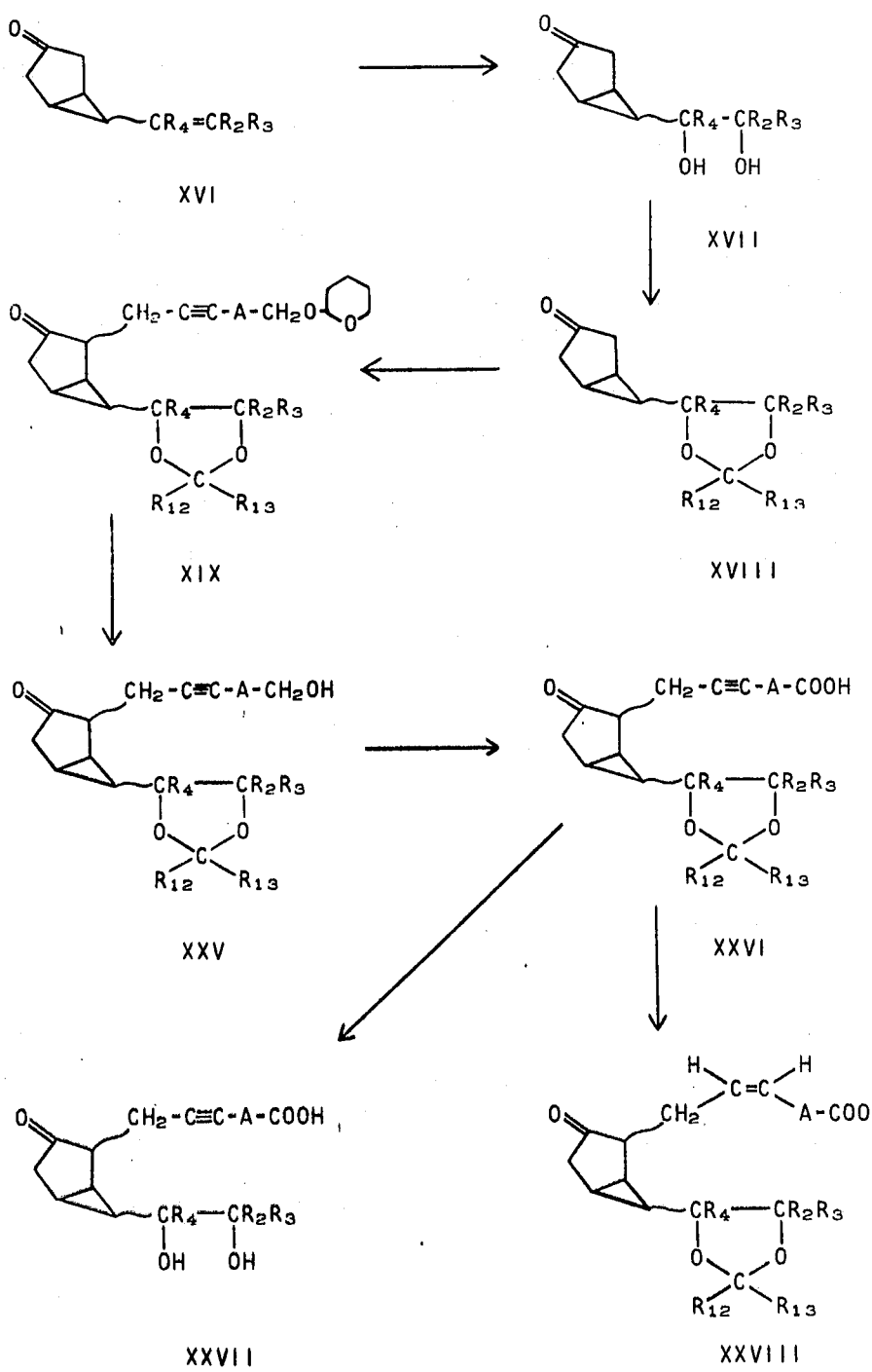

CHART C
Br-A-CH$_2$OH        XXIV
↓
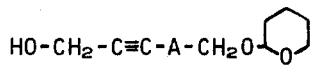        XXIII
HO-CH$_2$-C≡CH
↓
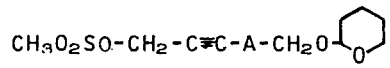        XXII
↓
CH$_3$O$_2$SO-CH$_2$-C≡C-A-CH$_2$O-⟨THP⟩        XXI
↓
Hal-CH$_2$-C≡C-A-CH$_2$O-⟨THP⟩        XX
CHART D
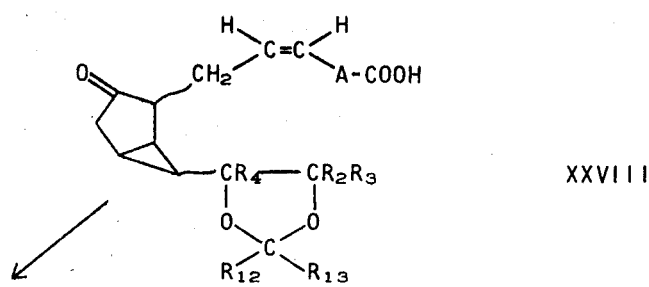        XXVIII
↓

CHART D -continued
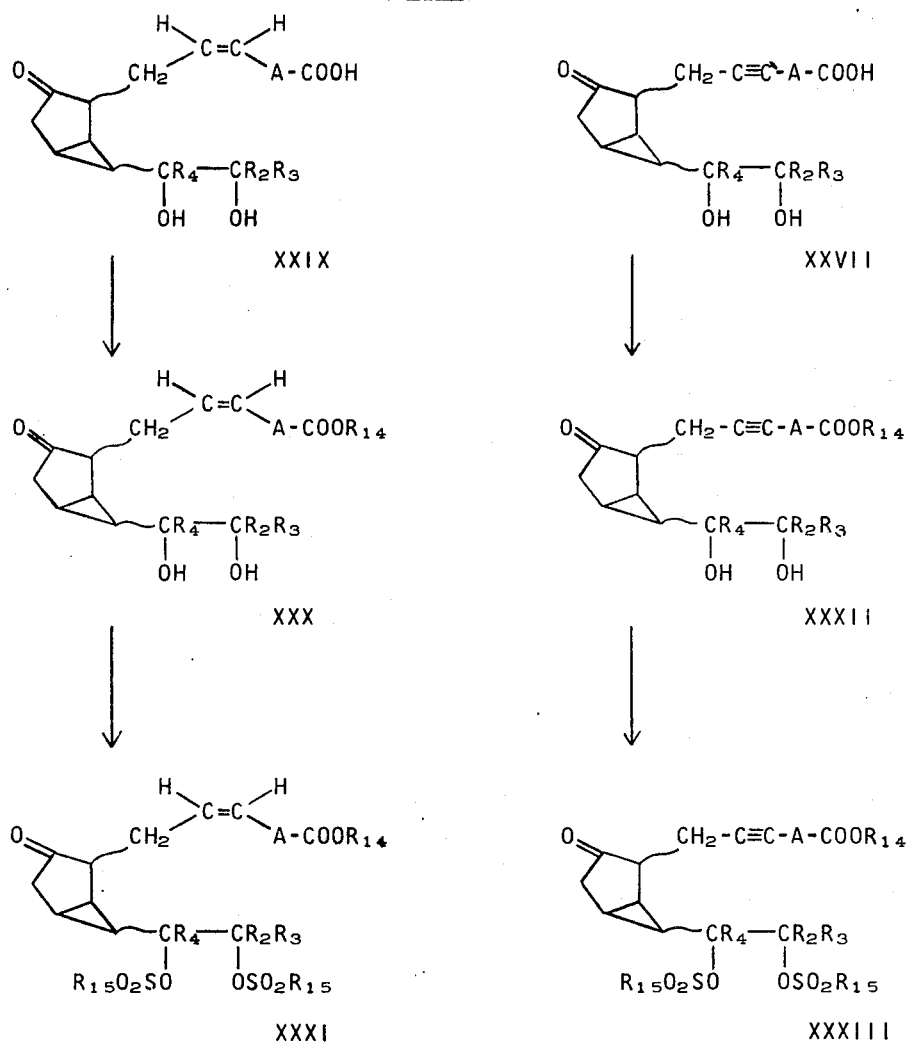
CHART E
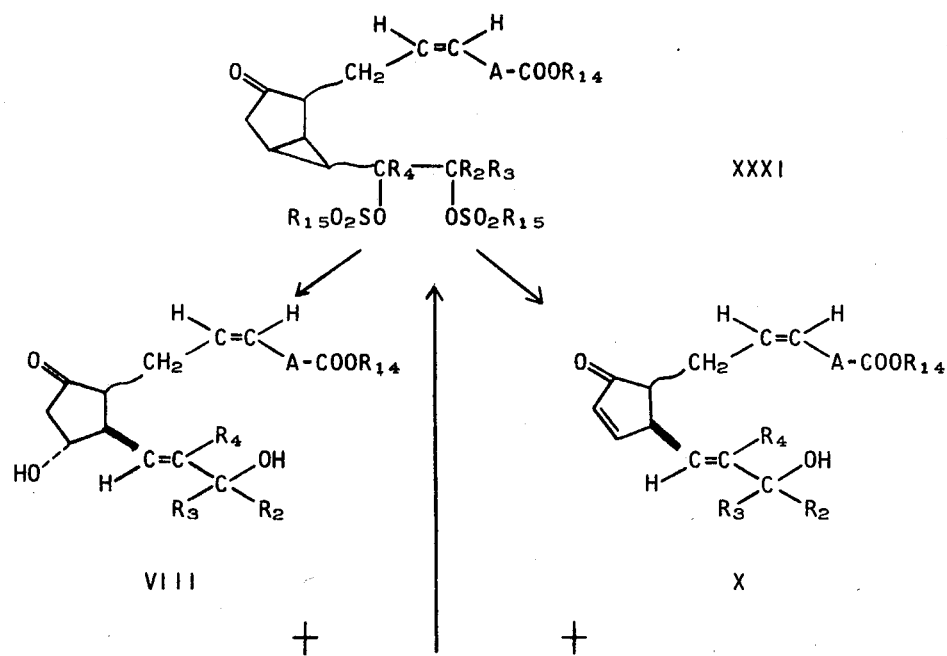

CHART E -continued
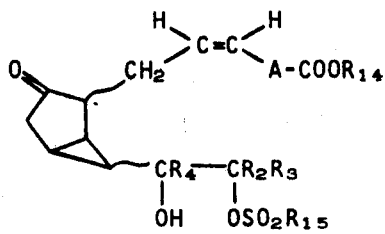
XXXIV
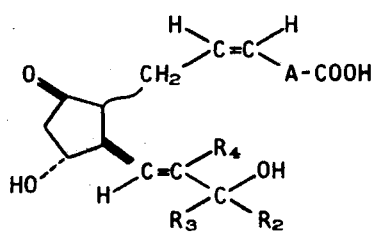
XXXV
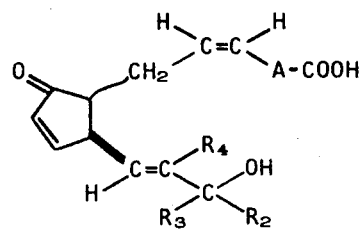
XXXVI
CHART F
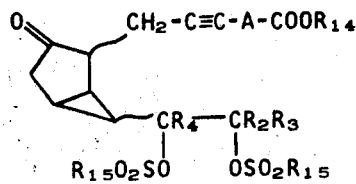
XXXIII
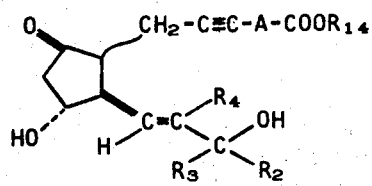
XII
+
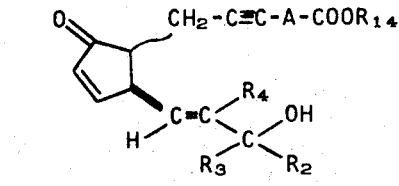
+
XIV

CHART F -continued

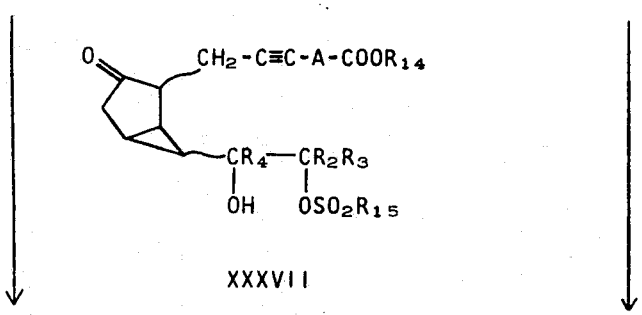

XXXVII

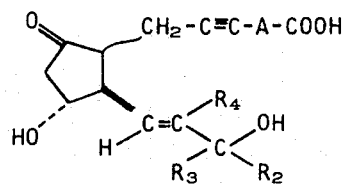

XXXVIII

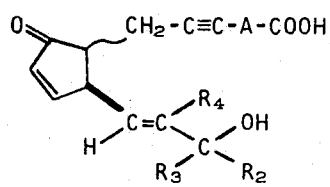

XXXIX

In those Charts, $R_1$, $R_2$, $R_3$, $R_4$, A, and ~ attached to the cyclophentane ring are as defined above. V is cis—CH=CH— or —C≡C—. $R_{12}$ and $R_{13}$ are alkyl of one to 4 carbon atoms, inclusive. $R_{14}$ is the same as $R_1$ except that $R_{14}$ does not include hydrogen. $R_{15}$ is alkyl of one to 5 carbon atoms, inclusive. The symbol ~ attached to the cyclopropane ring indicates exo or endo configuration for the moiety so attached.

The bicyclo-ketone of formula XVI in Chart B is the initial reactant in these multi-step processes. That ketone exists in four isomeric forms, exo and endo with respect to the attachment of the —CR$_4$=CR$_2$R$_3$ moiety, and cis and trans with respect to the double bond in that same moiety. Each of those isomers separately or various mixtures thereof are used as reactants according to this invention to produce substantially the same final PGE$_2$ type or 5,6-dehydro-PGE$_2$-type product mixture.

In exo configuration, the formula XVI keto is known to the art. See Belgian Pat. No. 702,477; reprinted in Farmdoc Complete Specifications, Book 714, No. 30,905, page 313, Mar. 12, 1968.

In that Belgian patent, the reaction sequence leading to exo ketone XVI is as follows: The hydroxy of 3-cyclopentenol is protected, for example, with a tetrahydropyranyl group. Then a diazoacetic acid ester is added to the double bond to give an exo-endo mixture of a bicyclo[3.1.0]hexane substituted at 3 with the protected hydroxy and at 6 with an esterified carboxyl. The exo-endo mixture is treated with a base to isomerize the endo isomer in the mixture to more of the exo isomer. Next, the carboxylate ester group at 6 is transfomed to an aldehyde group or ketone group,

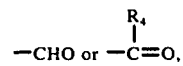

wherein $R_4$ is as defined above. Then, said aldehyde group or said keto group is transformed by the Wittig reaction to a moiety of the formula —CR$_4$=CR$_2$R$_3$ which is in exo configuration relative to the bicyclo ring structure, and is the same as shown in formula XVI. Next, the protective group is removed to regenerate the 3-hydroxy which is then oxidized, for example, by the Jones reagent, to give said exo ketone XVI.

Separation of the cis-exo and trans-exo isomers of XVI is described in said Belgian patent. However, as mentioned above, that separation is usually not necessary since the cis-trans mixture is useful as a reactant in the next process step.

The process described in said Belgian Pat. No. 702,477 for producing the exo form of bicyclo-ketone XVI uses as an intermediate, the exo form of a bicyclo[3.1.0]hexane substituted at 3 with a protected hydroxy, e.g., tetrahydropyranyloxy and at 6 with an esterified carboxyl. When the corresponding endo compound is substituted for that exo intermediate, the Belgian patent process leads to the endo form of bicyclo-ketone XVI. That endo intermediate used in the Belgian patent process has the formula:

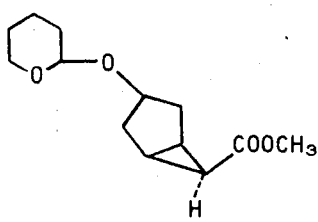

XL compound XL is prepared by reacting endo-bicyclo[3.1.0]hex-2-ene-6-carboxylic acid methyl ester with diborane in a mixture of tetrahydrofuran and diethyl ether, a reaction generally known in the art, to give endo-bicyclo[3.1.0]hexan-3-ol-6-carboxylic acid methyl ester which is then reacted with dihydropyran in the presence of a catalytic amount of $POCl_3$ to give the desired compound. This is then used as described in said Belgian patent to produce the endo form of bicyclo-ketone XVI.

As for exo XVI, this process produces a mixture of endo-cis and endo-trans. These are separated as described for the separation of exo-cis and exo-trans XVI, but this separation is usually not necessary since, as mentioned above, the cis-trans mixture is useful as a reactant in the next process step.

In the process of said Belgian Pat. No. 702,477, certain organic halides, e.g., chlorides and bromides, are necessary to prepare the Wittig reagents used to generate the generic moiety $—CR_4=CR_2R_3$ of bicyclo-ketone XVI. These organic chlorides and bromides

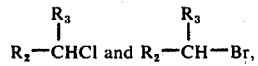

are knwon in the art or can be prepared by methods known in the art.

To illustrate the availability of these organic chlorides and bromides, consider the above-described special compounds of formula VIII, for example, wherein $R_2$ is $—(CH_2)_d—X$; wherein $d$ is zero, one, 2, 3, or 4, and X is isobutyl, tert-butyl, 3,3-difluorobutyl, 4,4-difluorobutyl, or 4,4,4-trifluorobutyl. The halides are advantageously prepared by reacting the corresponding primary alcohol, $R_2CH_2OH$, or secondary alcohol

wherein $R_3$ is as defined above, with $PCl_3$, $PBr_3$, or any of the other halogenating agents known to the art to be useful for this purpose.

In the case of X being isobutyl or tert-butyl, some of the necessary lower molecular weight primary alcohols, e.g., $(CH_3)_2CHCH_2CH_2OH$ and $(CH_3)_3CCH_2OH$, are known. The remainder of the alcohols are prepared by reacting the bromides corresponding to those known alcohols with sodium cyanide, hydrolyzing the resulting nitriles to the corresponding carboxylic acids, and then reducing those acids to the corresponding primary alcohols with lithium aluminum hydride, thus extending the carbon chain one carbon atom at a time until all primary alcohols are prepared. The corresponding secondary alcohols,

are prepared by transforming the —COOH of the corresponding carboxylic acid, all of which are known or prepared as just described, to

by known procedures, for example, $R_2COCl + (R_3)_2Cd$, the resulting ketone then being reduced to the secondary alcohol with sodium borohydride.

In the case of X being 3,3-difluorobutyl, the necessary alcohols are prepared from ketocarboxylic acids of the formula, $CH_3—CO—(CH_2)_n—COOH$, wherein n is 2, 3, 4, 5, or 6. All of those acids are known. The methyl esters are prepared and reacted with sulfur tetrafluoride to produce the corresponding $CH_3—CF_2—(CH_2)_n—COOCH_3$ compounds, which are then reduced with lithium aluminum hydride to $CH_3—CF_2—(CH_2)_n—CH_2OH$, or transformed as described above to

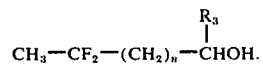

These alcohols are then transformed to the bromide or chloride by reaction with $PBr_3$ or $PCl_3$.

In the case of X being 4,4-difluorobutyl, the initial reactants are the known dicarboxylic acids, $HOOC—(CH_2)_f—COOH$, wherein $f$ is 3, 4, 5, 6, or 7. These dicarboxylic acids are esterified to $CH_3OOC—(CH_2)_f—COOCH_3$ and then half saponified, for example with barium hydroxide, to give $HOOC—(CH_2)_f—COOCH_3$. The free carboxyl group is transformed first to the acid chloride with thionyl chloride and then to an aldehyde by the Rosenmund reduction. Reaction of the aldehyde with sulfur tetrafluoride then gives $CHF_2—(CH_2)_f—COOCH_3$ which by successive treatment with lithium aluminum hydride and $PBr_3$ or $PCl_3$ gives the necessary bromides or chlorides, $CHF_2—(CH_2)_f—CH_2Br$ or $CHF_2—(CH_2)_f—CH_2Cl$. Those formulas can be rewritten as $CHF_2CH_2CH_2CH_2(CH_2)_d—CH_2Br$ or $CHF_2CH_2CH_2CH_2(CH_2)_d—CH_2Cl$. Corresponding secondary alcohols are prepared as described above.

In the case of X being 4,4,4-trifluorobutyl, aldehydes of the formula $CH_3OOC—(CH_2)_f—CHO$ are prepared as described above. Reduction of the aldehyde with sodium borohydride gives the alcohol $CH_3OOC—(CH_2)_f—CH_2OH$. Reaction with $PBr_3$ or $PCl_3$ then gives $CH_3OOC—(CH_2)_f—CH_2—X$, wherein X is Br or Cl. Saponification of that ester gives the carboxylic acid which by reaction with sulfur tetrafluoride gives the necessary $CF_3—(CH_2)_f—CH_2—Br$ or $CF_3—(CH_2)_f—CH_2—Cl$. Corresponding secondary alcohols are prepared by transforming $CH_3OOC—(CH_2)_f—CHO$ to $CH_3OOC—(CH_2)_f—COCH_3$ by known methods, and then proceeding with that ketone as described above for the aldehyde.

For the above reactions of $SF_4$, see U.S. Pat. No. 3,211,723 and J. Org. Chem. 27, 3164 (1962).

The transformation of bicyclo-ketone-olefin XVI to glycol XVII (chart B) is carried out by reacting olefin XVI with a hydroxylation reagent. Hydroxylation reagents and procedures for this purpose are known in the art. See, for example, Gunstone, Advances in Organic Chemistry, Vol. 1, pp. 103–147, Interscience Publishers, New York, N.Y. (1960). Various isomeric glycols are obtained depending on whether olefin XVII is cis or trans and endo or exo, and on whether a cis or a trans hydroxylation reagent is used. Thus endo-cis olefin XVI gives a mixture of two isomeric erythro glycols of formula XVII with a cis hydroxylation agent, e.g., osmium tetroxide. Similarly, the endo-trans olefin XVI gives a similar mixture of the same two erythro glycols with a trans hydroxylation agent, e.g., hydrogen peroxide. The endo-cis olefins and the endo-trans olefins XVI give similar mixtures of two threo isomers with cis and trans hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Charts B, C, E, and F to produce final products of formulas VIII and XII, and then, according to Chart A, to produce the other final products of this invention. Thus the various isomeric glycol mixtures encompassed by formula XVII produced from the various isomeric olefins encompassed by formula XVI are all useful for these same purposes.

The transformation of glycol XVII to the cyclic ketal of formula XVIII (Chart B) is carried out by reacting said glycol with a dialkyl ketone of the formula

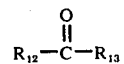

wherein $R_{12}$ and $R_{13}$ are alkyl of one to 4 carbon atoms, inclusive, in the presence of an acid catalyst, for example potassium bisulfate or 70% aqueous perchloric acid. A large excess of the ketone and the absence of water is desirable for this reaction. Examples of suitable dialkyl ketones are acetone, methyl ethyl ketone, diethyl ketone, methyl propyl ketone, and the like. Acetone is preferred as a reactant in this process.

The transformation of cyclic ketal XVIII to cyclic ketal XIX is carried out by alkylating ketal XVIII with an acetylenic alkylating agent of formula XX (Chart C), wherein A is as defined above, and Hal is chlorine, bromine, or iodine.

Any of the alkylation procedures known in the art to be useful for alkylating cyclic ketones with alkyl halides, especially haloalkanoic esters are used for the transformation of XVIII to XIX. See, for example, the above mentioned Belgian Pat. No. 702,477 for procedures useful here and used there to carry out similar alkylations.

For this alkylation, it is preferred that Hal be bromo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Especially preferred is potassium tert-butoxide. Preferred diluents for this alkylation are tetrahydrofuran and 1,2-dimethoxyethane. Otherwise, procedures for producing and isolating the desired formula XIX compound are within the skill of the art.

This alkylation procedure produces a mixture of alpha and beta alkylation products, i.e., a mixture of formula XIX products wherein part has the

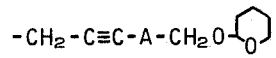

moiety attached in alpha configuration and wherein part has that moiety attached in beta configuration. When about one equivalent of base per equivalent of formula XVIII ketone is used, the alpha configuration usually predominates. Use of an excess of base and longer reaction times usually result in production of larger amounts of beta products. These alpha-beta isomer mixtures are separated at this stage or at any subsequent stage in the multi-step processes shown in Charts D, E, and F. Silica gel chromatography is preferred for this separation.

The alkylating agent of formula XX is prepared by the series of reactions shown in Chart C. The initial reactants, $Br—A—CH_2OH$, are omega bromoalcohols which are known in the art or can be prepared by methods known in the art. For example, when A in the final product is to be trimethylene as it is in racemic $PGE_2$ and 5,6-dehydro-$PGE_2$, the necessary 4-bromobutanol is prepared by reacting tetrahydrofuran with hydrogen bromide.

To illustrate the availability of the other bromoglycols of formula XXIV (Chart C), consider the above-described special compounds of formula VIII, wherein A is $—(CH_2)_b—Z—$, wherein $b$ is zero, one, 2, or 3, and Z is ethylene substituted by one or 2 fluoro, methyl, or ethyl, or by one alkyl of 3 or 4 carbon atoms. These omega-bromoalcohols, $Br—(CH_2)_b—Z—CH_2OH$, are prepared by starting with the appropriate succinic acid, $HOOC—Z—COOH$, all of which are known or easily accessible by known methods. These succinic acids are transformed to the corresponding anhydrides by known procedures. Each anhydride is then reacted with an alkanol, for example, methanol, to give the corresponding succinic acid half ester, e.g., $HOOC—Z—COOCH_3$. When Z is unsymmetrical, e.g., substituted with one fluoro, a mixture of isomeric half esters is obtained, $HOOC—Z—COOCH_3$ and $CH_3—OOC—Z—COOH$, which is separated to give the desired isomer.

When it is desired that $b$ in $Br—(CH_2)_b—Z—CH_2OH$ be zero, the succinic acid half ester is subjected to the Hunsdiecker reaction, thereby producing $Br—Z—COOCH_3$, which is reduced by lithium aluminum hydride to $Br—Z—CH_2OH$. When $b$ is to be one, the carboxyl group of the succinic acid half ester is changed to acid chloride with thionyl chloride, to aldehyde by the Rosenmund reduction, to alcohol with sodium borohydride, and to $—CH_2Br$ with $PBr_3$, giving $Br—CH_2—Z—COOCH_3$, which is then reduced to $Br—CH_2—Z—CH_2OH$ with lithium aluminum hydride. When $b$ is to be 2 or 3, the succinic acid half ester is subjected once or twice to the Arndt-Eistert reaction to produce $HOOC—CH_2—Z—COOCH_3$ or HOO- C—$CH_2CH_2$—Z—$COOCH_3$, which is then subjected to the same series of reactions given above to give Br—$CH_2CH_2$—Z—$CH_2OH$ or Br—$CH_2CH_2$—Z—$CH_2OH$.

Referring again to Chart C, the several process steps, XXIV to XXIII, XXIII to XXII, XXII to XXI, and XXI to XX are exemplified hereinafter in the case wherein A is trimethylene. Those procedures are used when A is other than trimethylene and within the scope of A as defined above.

The transformation of alkylation product XIX to primary alcohol XXV (Chart B) is carried out by treating the tetrahydropyranyl ether XIX with any strong acid under such conditions that the cyclic acetal group remains intact. Hydrolysis of tetrahydropyranyl ethers under such conditions is well known to those skilled in the art. Oxalic acid is especially preferred for this acid hydrolysis of XIX to XXV.

The oxidation of primary alcohol XXV to carboxylic acid XXVI (Chart B) is carried out by oxidizing XXV with any oxidizing agent which will not also attack the acetylenic linkage in XXV. An especially useful reagent for this purpose is the Jones reagent, i.e., acidic chromic acid. See J. Chem. Soc. 39 (1946). Acetone is a suitable diluent for this purpose, and a slight excess of oxidant and temperatures at least as low as about 0° C., preferably about −10° to about −20° C. should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. Chem. Cos. 87, 5661 (1965).

As shown on Charts B, D, and E, carboxylic acid XXVI leads to $PG_2$-type compounds (Chart E) or 5,6-dehydro-$PG_2$-type compounds (Chart E) depending on whether the —C≡C— bond of XXVI is reduced to cis—CH=CH—. When a $PG_2$-type compound is desired, XXVI is reduced to cis-olefin XXVIII (Chart B) with hydrogen and a catalyst which catalyzes hydrogenation of —C≡C— only to cis—CH=CH—. Such catalysts and procedures are well known to the art. See, for example, Fieser et al., "Reagents for Organic Synthesis", pp. 566–567; John Wiley & Sons, Inc., New York, N.Y. (1967). Palladium (5%) on barium sulfate, especially in the presence of pyridine as a diluent, is a suitable catalyst for this purpose.

The transformations of cyclic ketals XXVI and XVIII to glycols XXVII and XXIX, respectively, (Charts B and D) are carried out by reacting the cyclic ketal with an acid with pK less than 5. Suitable acids and procedures for hydrolyzing cyclic ketals to glycols are known in the art. Suitable acids are formic acid and hydrochloric acid. Especially preferred as a diluent for this reaction is tetrahydrofuran.

The transformations of glycol-acids XXIX and XXVII to glycol-esters XXX and XXXII, respectively, (Chart D) are esterifications carried out by procedures known in the art to be useful for transforming carboxylic acids to esters —$COOR_{14}$ wherein $R_{14}$ is as defined above. For example, a diazohydrocarbon, e.g., diazomethane, advantageously in diethyl ether solution, is reacted with the acid to produce the ester, e.g., the methyl ester, by known procedures. When $R_{14}$ is ethyl substituted with 3 chloro, 2 or 3 bromo, or 1, 2, or 3 iodo, the glycol acid is reacted with the appropriate haloethanol, e.g., β,β,β-trichloroethanol when $R_4$ is to be —$CH_2CCl_3$, in the presence of a carbodiimide, e.g., dicyclohexylcarbodiimide, and a base, e.g., pyridine. This mixture, advantageously with an inert diluent, e.g., dichloromethane, usually produces the desired haloethyl ester within several hours at about 25° C. The other esters within the scope of $R_{14}$ in formulas XXX and XXXII are prepared by procedures known to the art.

The bis-alkanesulfonic acid esters XXXI and XXXIII (Chart D) are prepared by reacting glycol-esters XXX and XXXII, respectively, with an alkylsulfonyl chloride or bromide, or with an alkanesulfonic acid anhydride, the alkyl in each containing one to 5 carbon atoms, inclusive. Alkylsulfonyl chlorides are preferred for this reaction. The reaction is carried out in the presence of a base to neutralize the byproduct acid. Especially suitable bases are tertiary amines, e.g., dimethylaniline or pyridine. It is usually sufficient merely to mix the two reactants and the base, and maintain the mixture in the range 0° to 25° C. for several hours. The formula XXXI and XXXIII bis-sulfonic acid esters are then isolated by procedures known to the art.

Referring now to Chart E, bis-sulfonic acid esters XXXI are transformed either by $PGE_2$-type compounds VIII or to $PGA_2$-type compounds X. Referring to Chart F, bis-sulfonic acid esters XXXIII are transformed either to 5,6-dehydro-$PGE_2$-type compounds XII or to 5,6-dehydro-$PGA_2$-type compounds XIV.

The transformations of XXXI and XXXIII to VIII and XII, respectively, are carried out by reacting XXXI and XXXIII with water in the range about 0° to about 60° C. In making racemic $PGE_2$ or 5,6-dehydro-$PGE_2$, usually 25° C. is a suitable reaction temperature, the reaction then proceeding to completion in about 5 to 10 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of formula VIII or formula XII isomers which differ in the configuration of the side chain hydroxy, that being either R or S. These are separated from byproducts and from each other by silica gel chromatography. A usual byproduct is the mono-sulfonic acid ester of formula XXXIV (Chart E) or formula XXXVII (Chart F). This mono-sulfonic acid ester is esterified to the formula XXXI or XXXIII bis-sulfonic acid ester in the same manner described above for the transformation of glycol XXX or XXXII to bis-ester XXXI or XXXIII, and thus is recycled back to additional formula VIII or XII final product.

For the transformation of bis-esters XXXI and XXXIII to final products VIII and XIII, respectively, it is preferred to use the bis-mesyl esters, i.e., compounds XXXI and XXXIII wherein $R_{15}$ is methyl.

The configuration of the —$CH_2$—CH=λCH—A—$COOR_{14}$ moiety in the formula XXXI bis-ester and the configuration of the —$CH_2$—C≡C—A—$COOR_{14}$ moiety in the formula XXXIII bis ester do not change during these transformations of XXXI to VIII or XXXIII to XII. Therefore, when in formula XXXI, $R_2$ is pentyl, $R_3$ and $R_4$ are hydrogen, and A is trimethylene, racemic $PGE_2$ esters are obtained when the —CH$_2$CH=CH—A—COOR$_{14}$ is attached initially in alpha configuration, and racemic 8-iso-PGE$_2$ esters are obtained when that moiety is attached in beta configuration. Similarly, when in formula XXXIII, R$_2$ is pentyl, R$_3$ and R$_4$ are hydrogen, and A is trimethylene, 5,6-dehydro-PGE$_2$ esters are obtained when the —CH$_2$—C≡C—A—COOR$_{14}$ moiety is attached initially in alpha configuration, and 8-iso-5,6-dehydro-PGE$_2$ esters are obtained when that moiety is attached in beta configuration.

Referring again to Charts E and F, the transformations of bis-sulfonic acid esters XXXI and XXXIII to formula X PGA$_2$-type compounds and formula XIV 5,6-dehydro-PGA$_2$-type compounds, respectively, is carried out by heating the formula XXXI or formula XXXIII bis-ester in the range 40° to 100° C. with a combination of water, a base characterized by its water solution having a pH 8 to 12, and sufficient inert water-soluble organic diluent to form a basic and substantially homogenous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for the transformation of bis-esters XXXI and XXXIII to final products VIII and XII. The same mono-sulfonic acid esters XXXIV and XXXVII observed as byproducts in those transformations are also observed during preparation of final products X and XIV. Also, as for the production of VIII and XII the bis-mesyl esters of XXXI and XXXIII are preferred when making X and XIV. Also as for the production of VIII and XII, during production of X and XIV, alpha XXXI and alpha XXXIII give alpha X and alpha XIV, respectively, beta XXXI and beta XXXIII give beta X and beta XIV, respectively, and in each case, alpha and beta X and XIV, a mixture of R and S isomers is obtained. These R and S isomer mixtures are separated by silica gel chromatograph.

The formula VIII, X, XII, and XIV produced according to the processes outlined in Charts B, C, D, E, and F and discussed above are all R$_{14}$ carboxylic acid esters, wherein R$_{14}$ is as described above. Moreover, when these compounds are used to produce compounds of formulas IX, XI, XIII, and XV according to the processes outlined in Chart A and discussed above, corresponding R$_{14}$ esters are likely to be produced, especially in the case of the PGF$_2$ and 5,6-dehydro-PGF$_2$ compounds of formulas IX and XIII, respectively. For some of the uses described above, it is preferred that these formula VIII to XV compounds be in free acid form, or in salt form which requires the free acid as a starting material. The formula IX, XI, XIII, and XV R$_{14}$ esters are easily hydrolyzed or saponified by the usual known procedures, especially when R$_{14}$ is alkyl of one to 4 carbon atoms, inclusive. Therefore it is preferred when the free acid form of compounds IX, XI, XIII, and XV is desired, that R$_{14}$ be such alkyl, especially methyl or ethyl.

On the other hand, the formula VIII, X, XII, and XIV final products are difficult to hydrolyze or saponify without unwanted structural changes in the desired acids. There are two other procedures useful to make the free acid form of formula VIII, X, XII, and XIV products.

One of those procedures is applicable mainly in preparing the free acids from the corresponding alkyl esters wherein the alkyl group contains one to 8 carbon atoms, inclusive. That procedure comprises subjecting the alkyl ester corresponding to formula VIII, X, XII, or XIV to the acylase enzyme system of a microorganism species of Subphylum 2 of Phylum 111, and thereafter isolating the acid. Especially preferred for this purpose are species of the orders Mucorales, Hypocreales, Moniliales, and Actinomycetales. Also especially preferred for this purpose are species of the families Mucoraceae, Cunninghamellaceae, Nectreaceae, Moniliaceae, Dematiaceae, Tuberculariaceae, Actinomycetaceae, and Streptomycetaceae. Also especially preferred for this purpose are species of the genera Absidia, Circinella, Gongronella, Rhizopus, Cunninghamella, Calonectria, Aspergillus, Penicillium, Sporotrichum, Cladosporium, Fusarium, Nocardia, and Streptomyces.

Examples of microorganisms falling within the scope of those preferred orders, families, and genera are listed in U.S. Pat. No. 3,290,226.

This enzymatic ester hydrolysis is carried out by shaking the formula VIII, X, XII, or XIV alkyl ester in aqueous suspension with the enzyme contained in a culture of one of the above-mentioned microorganism species until the ester is hydrolyzed. A reaction temperature in the range 20° to 30° C. is usually satisfactory. A reaction time of one to 20 hours is usually sufficient to obtain the desired hydrolysis. Exclusion of air from the reaction mixture, for example, with argon or nitrogen is usually desirable.

The enzyme is obtained by harvest of cells from the culture, followed by washing and resuspension of the cells in water, and cell disintegration, for example, by stirring with glass beads or by sonic or ultrasonic vibrations. The entire aqueous disintegration mixture is used as a source of the enzyme. Alternatively and preferably, however, the cellular debris is removed by centrifugation or filtration, and the aqueous supernatant or filtrate is used.

In some cases, it is advantageous to grow the microorganism culture in the presence of an alkyl ester of an aliphatic acid, said acid containing 10 to 20 carbon atoms, inclusive, and said alkyl containing one to 8 carbon atoms, inclusive, or to add such an ester to the culture and maintain the culture without additional growth for one to 24 hours before cell harvest. Thereby, the enzyme produced is sometimes made more effective in transforming the formula VIII, X, XII, or XIV ester to the free acid. An example of a useful alkyl ester for this purpose is methyl oleate.

Although, as mentioned above, most of the R$_{14}$ esters encompassed by formulas VIII, X, XII, and XIV are not easily hydrolyzed or saponified to the corresponding free acids, certain of those esters are transformed to free acids by another method. Those esters are the haloethyl esters wherein R$_{14}$ is —CH$_2$CCl$_3$, are transformed to free acids by treatment with zinc metal and an alkanoic acid of 2 to 6 carbon atoms, preferably acetic acid. Zinc dust is preferred as the physical form of the zinc. Mixing the haloethyl ester with the zinc dust at about 25° C. for several hours usually causes substantially complete replacement of the haloethyl moiety of the formula VIII, X, XII, or XIV ester with hydrogen. The free acid is then isolated from the reaction mixture by procedures known to the art. This procedure is also applicable to the production of the free acid form of the formula IX, XI, XIII and XV compounds from the corresponding haloethyl esters thereof.

The preparation of these haloethyl esters is described above during the discussion of the esterification of acids XXIV and XXVII to esters XXX and XXXII, respectively.

As described above, the alkylation of cyclic ketal-ketone XVIII to ketone XIX (Chart B) usually produces a mixture of alpha and beta alkylation products with respect to the

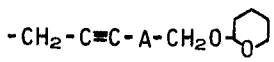

moiety. Also as described above, those two isomers lead to different final products, alpha leading to the $PG_2$-series and beta leading to the 8-iso-$PG_2$-series. If a compound in one or the other of those series is preferred, there are two methods for favoring production of the preferred final product.

One of those methods involves isomerization of the final product of formula VIII or formula XII wherein $R_{14}$ is as defined above or hydrogen. Either the alpha isomer of formula VIII or XII, or the beta isomer of formula VIII or XII is maintained in an inert liquid diluent in the range 0° to 80° C. and in the presence of a base characterized by its water solution having a pH below about 10 until a substantial amount of the isomer has been isomerized to the other isomer, i.e., alpha to beta or beta to alpha. Preferred bases for this purpose are the alkali metal salts of carboxylic acids, especially alkanoic acids of 2 to 4 carbon atoms, e.g., sodium acetate. Examples of useful inert liquid diluents are alkanols of one to 4 carbon atoms, e.g., ethanol. This reaction at about 25° takes about one to about 20 days. Apparently an equilibrium is established. The mixtures of the two isomers, alpha and beta, are separated from the reaction mixture by known procedures, and then the two isomers are separated from each other by known procedures, for example, chromatography, recrystallization, or a combination of those. The less preferred isomer is then subjected to the same isomerization to produce more of the preferred isomer. In this manner, by repeated isomerizations and separations, substantially all of the less preferred isomer of the formula VIII or formula XII compound is transformed to more preferred isomer.

The second method for favoring production of a preferred final formula VIII or formula XII isomer involves any one of the intermediates of formulas XIX, XXV, XXVI, XXVII, XXVIII, XXIX, XXX, or XXXII (Charts B and D). Either the alpha form or the beta form of one of those intermediates is transformed to a mixture of both isomers by maintaining one or the other isomer, alpha or beta, in an inert liquid diluent in the presence of a base and in range 0° to 100° C. until a substantial amount of the starting isomer has been isomerized to the other isomer. Preferred bases for this isomerization are alkali metal amides, alkali metal alkoxides, alkali metal hydrides, and triarylmethyl alkali metals. Especially preferred are alkali metal tert-alkoxides of 4 to 8 carbon atoms, e.g., potassium tert-butoxide. This reaction at about 25° C. proceeds rapidly (one minute to several hours). Apparently an equilibrium mixture of both isomers is formed, starting with either isomer. The isomer mixtures in the equilibrium mixture thus obtained are isolated by known procedures, and then the two isomers are separated from each other by known procedures, for example, chromatography. The less preferred isomer is then subjected to the same isomerization to produce more of the preferred isomer. In this manner, by repeated isomerizations and separations, substantially all of the less preferred isomer of any of these intermediates is transformed to the more preferred isomer. Cyclic acetalketone intermediates XIX and XXV are preferred over intermediates for this isomerization procedure.

The final formula VIII to XV compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula VIII to XV acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VIII to XV acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VIII to XV acid with the stoichiometric amount of the corresponding quaternary ammonium hydroxide in water solution, followed by evaporation of the water.

The invention can be more fully understood by the following examples and preparations:

All temperatures are in degrees centigrade.

Infrared absorption spectra are recorded on a PerkinElmer model 421 infrared spectrophotometer. Except when specified otherwise, undiluted (neat) samples are used.

NMR spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

Preparation 1

Endo-bicyclo[3.1.0]hexan-3-ol-6-carboxylic acid methyl ester

A mixture of endo-bicyclo[3.1.0]hex-2-ene-6-carboxylic acid methyl ester (103 g.) and anhydrous diethyl ether (650 ml.) is stirred under nitrogen and cooled to −5° C. A one molar solution (284 ml.) of diborane in tetrahydrofuran is added dropwise during 30 minutes while keeping the temperature below 0° C. The resulting mixture is then stirred and allowed to warm to 25° C. during 3 hours. Evaporation under reduced pressure gives a residue which is dissolved in 650 ml. of anhydrous diethyl ether. The solution is cooled to 0° C., and 3 normal aqueous sodium hydroxide solution (172 ml.) is added dropwise under nitrogen and with vigorous stirring during 15 minutes, keeping the temperature at 0° to 5° C. Next, 30% aqueous hydrogen peroxide (94 ml.) is added dropwise with stirring during 30 minutes at 0° to 5° C. The resulting mixture is stirred an hour while warming to 25° C. Then, 500 ml. of saturated aqueous sodium chloride solution is added, and the diethyl ether layer is separated. The aqueous layer is washed with four 200 ml. portions of ethyl acetate, the washings being added to the diethyl ether layer, which is then washed with saturated aqueous sodium chloride solution, dried, and evaporated to give 115 g. of a residue. This residue is distilled under reduced pressure to give 69 g. of a mixture of the methyl esters of endo-bicyclo[3.1.0]hexan-3-ol-6-carboxylic acid and endo-bicyclo[3.1.0]hexan-2-ol-6-carboxylic acid; b.p. 86°–95° C. at 0.5 mm.

Preparation 2

Endo-bicyclo[3.1.0]hexan-3-ol-6-carboxylic acid methyl ester tetrahydropyranyl ether The 2-ol and 3-ol mixture (66 g.) obtained according to Preparation 1 in 66 ml. of dihydropyran is stirred and cooled at 15°–20° C. during addition of 3 ml. of anhydrous diethyl ether saturated with hydrogen chloride. The temperature of the mixture is then kept in the range 20° to 30° C. for one hour with cooling, and is then kept at 25° for 15 hours. Evaporation gives a residue which is distilled under reduced pressure to give 66 g. of a mixture of the methyl esters-tetrahydropyranyl ethers of endo-bicyclo[3.1.0]hexan-3-ol-6-carboxylic acid and endo-bicyclo[3.1.0]hexan-2-ol-6-carboxylic acid; b.p. 96°–104° C. at 0.1 mm.

Preparation 3

Endo-6-hydroxymethylbicyclo[3.1.0]hexan-3-ol-3-tetrahydropyranyl ether

A solution of the mixture (69 g.) of products obtained according to Preparation 2 in 300 ml. of anhydrous diethyl ether is added dropwise during 45 minutes to a stirred and cooled mixture of lithium aluminum hydride (21 g.) in 1300 ml. of anhydrous diethyl ether under nitrogen. The resulting mixture is stirred 2 hours at 25° C., and is then cooled to 0° C. Ethyl acetate (71 ml.) is added, and the mixture is stirred 15 minutes. Water (235 ml.) is then added, and the diethyl ether layer is separated. The water layer is washed twice with diethyl ether and twice with ethyl acetate. A solution of Rochelle salts is added to the aqueous layer, which is then saturated with sodium chloride and extracted twice with ethyl acetate. All diethyl ether and ethyl acetate solutions are combined, washed with saturated aqueous sodium chloride solution, dried, and evaporated to give 61 g. of a mixture of the 3-tetrahydropyranyl ethers of endo-6-hydroxymethylbicyclo[3.1.0]hexan-3-ol and endo-6-hydroxmethyl-bicyclo[3.1.0]hexan-2-ol.

Preparation 4

Endo-bicyclo[3.1.0]hexan-3-ol-6-carboxaldehyde 3-tetrahydropyranyl ether

A solution of the mixture (34 g.) of products obtained according to Preparation 3 in 1000 ml. of acetone is cooled to −10° C. Jones reagent (75 ml. of a solution of 21 g. of chromic anhydride, 60 ml. of water, and 17 ml. of concentrated sulfuric acid), precooled to 0° C., is added dropwise with stirring during 10 minutes at −10° C. After 10 minutes of additional stirring at −10° C., isopropyl alcohol (35 ml.) is added during 5 minutes, and stirring is continued for 10 minutes. The reaction mixture is then poured into 8 l. of an ice and water mixture. The resulting mixture is extracted 6 times with dichloromethane. The combined extracts are washed with aqueous sodium bicarbonate solution, dried, and evaporated to give 27 g. of a mixture of the tetrahydropyranyl ethers of endo-bicyclo-[3.1.0]hexan-3-ol-6-carboxaldehyde and endo-bicyclo[3.1.0]hexan-2-ol-6-carboxaldehyde.

Preparation 5

Endo-6-(cis-and trans-1-heptenyl)-bicyclo[3.1.0]hexan-3-ol tetrahydropyranyl ether A mixture of hexyl bromide (100 g.), triphenylphosphine (160g.), and toluene (300 ml.) is stirred and heated at reflux for 7 hours. The mixture is then cooled to 10° C., and the crystals which separate are collected by filtration, washed with toluene, and dried to give 147 g. of hexyltriphenylphosphonium bromide; m.p. 197°–200° C.

A mixture of hexyltriphenylphosphonium bromide (102 g.) and benzene (1200 ml.) is stirred under nitrogen during addition of a solution of butyl lithium in hexane (146 ml. of a 15% solution – w/v). The resulting mixture is stirred 30 minutes. Then a solution of the mixture (27g.) of products obtained according to Preparation 4 in 300 ml. of benzene is added dropwise with stirring during 30 minutes. The mixture is heated and stirred at 70° C. for 2.5 hours, and then is cooled to 25° C. The resulting precipitate is collected by filtration and washed with benzene. The filtrate and benzene wash are combined, washed with water, dried, and evaporated to give 58 g. of a mixture of the tetrahydropyranyl ethers of endo-6-(cis- and trans-1-heptenyl)-bicyclo[3.1.0]hexan-3-ol and endo-6-(cis and trans-1-heptenyl)-bicyclo[3.1.0]hexan-2-ol.

Preparation 6

Endo-6-(cis- and trans-1-heptenyl)-bicyclo[3.1.0]hexan-3-ol

Oxalic acid (3 g.) is added to a solution of the mixture (58 g.) of products obtained according to Preparation 5 in 1500 ml. of methanol. The mixture is heated under reflux with stirring for 1.5 hours. Evaporation under reduced pressure gives an oil which is dissolved in dichloromethane. That solution is washed with aqueous sodium bicarbonate solution, dried, and evaporated under reduced pressure. The residue is dissolved in an isomeric hexane mixture (Skellysolve B), and chromatographed on 600 g. of wet-packed silica gel. The column is eluted with 2 l. of Skellysolve B, and then successively with 1 l. of 2.5%, 2 l. of 5%, 2 l. of 7.5%, 5 l. of 10%, and 3 l. of 15% ethyl acetate in Skellysolve B. Evaporation of the combined fractions corresponding to the 10% and 15% ethyl acetate gives 16 g. of a mixture of endo-6-(cis- and trans-1-heptenyl)-bicyclo[3.1.0]hexan-3-ol and endo-6-(cis- and trans-1-heptenyl)-bicyclo[3.1.0]hexan-2-ol.

Preparation 7

Endo-6-(cis- and trans-1-heptenyl)-bicyclo[3.1.0]hexan-3-one (formula XVI: $R_2$ is pentyl, $R_3$ and $R_4$ are hydrogen, ~ is endo)

A solution of the mixture (15 g.) of products obtained according to Preparation 6 in 450 ml. of acetone is cooled to −10° C. and stirred while adding 30 ml. of Jones reagent (Preparation 4) dropwise during 10 minutes. The resulting mixture is stirred 10 minutes at −10° C. Then, isopropyl alcohol (15 ml.) is added, and stirring is continued for 10 minutes. The mixture is poured into 2400 ml. of water. The water is extracted 5 times with dichloromethane. The combined extracts are washed with aqueous sodium bicarbonate solution, dried, and evaporated to give an oil. The oil is chromatographed on 500 g. of silica gel wet-packed with isomeric hexanes (Skellysolve B), eluting successively with 2 l. of Skellysolve B, 2 l. of 2.5% ethyl acetate in Skellysolve B, and 10 l. of 5% ethyl acetate in Skellysolve B. The first 1.5 l. of the 5% ethyl acetate in Skellysolve B eluate is evaporated to give 5.9 g. of endo-6-(cis- and trans-1-heptenyl)-bicyclo[3.1.0]hexan-3-one; $R_f$ 0.62 on thin layer chromatography with silica gel plates developed with 20% ethyl acetate in cyclohexane.

Following the procedures of Preparations 5, 6, and 7, but using in Preparation 5 butyl bromide, pentyl bromide, heptyl bromide, and octyl bromide in place of hexyl bromide, there are obtained the 1-pentenyl, 1-hexenyl, 1-octenyl, and 1-nonenyl compounds corresponding to the product of Preparation 7.

Also following the procedures of Preparations 5, 6, and 7, but using in Preparation 5, primary bromides of the formula X—(CH$_2$)$_d$—CH$_2$Br, wherein d is one, 2, 3, or 4, and X is isobutyl, tert-butyl, 3,3-difluorobutyl, 4,4-difluorobutyl, and 4,4,4-trifluorobutyl, in place of hexyl bromide, there are obtained compounds corresponding to the product of Preparation 7 with X—(CH$_2$)$_d$—CH=CH— in place of the 1-heptenyl moiety.

Also following the procedures of Preparations 5, 6, and 7 but using in Preparation 5 the other primary and secondary bromides of the formula

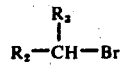

wherein $R_2$ and $R_3$ are as defined above in place of hexyl bromide, there are obtained compounds corresponding to the products of Preparation 7 with

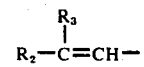

in place of the 1-heptenyl moiety.

Also following the procedures of Preparations 5, 6, and 7 but using in Preparation 5, bicyclo[3.1.0]hexane reactants with

in place of

wherein $R_4$ is defined above, there are obtained compounds corresponding to the product of Preparation 7 with

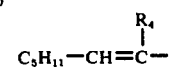

in place of the 1-heptenyl moiety. These different bicyclo[3.1.0]hexane reactants are prepared from the aldehyde product of Preparation 4 or the ester product of Preparation 3 by well known procedures. See, for example, the above-cited Belgian Pat. No. 702,477.

Also following the procedures of Preparations 5, 6, and 7 but using in Preparation 5, bicyclo[3.1.0]hexane reactants with

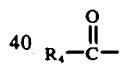

in place of

and also butyl bromide, pentyl bromide, heptyl bromide, octyl bromide, bromides of the formula X—(CH$_2$)$_d$—CH$_2$Br (as above defined), and primary and secondary bromides of the formula

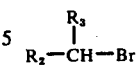

(as above defined), there are obtained compounds corresponding to the product of Preparation 7 with 1-pentenyl, 1-hexenyl, 1-octenyl, and 1-nonenyl, each substituted with $R_4$ at the 1-position, X—(CH$_2$)$_d$—CH=CR$_4$—, and

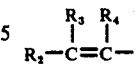

in place of the 1-heptenyl moiety.

Also following the procedures of Preparations 5, 6, and 7 but using in Preparation 5, exo-bicyclo[3.1.0-]hexane reactants in place of each of the endo reactants defined in Preparation 5 and after Preparation 7, the exo compound corresponding to the endo product of Preparation 7 and to each of the endo products defined after Preparation 7 are obtained. The necessary exo bicyclo[3.1.0]-hexane reactants are prepared as described in Belgian Pat. No. 702,477.

By the above-described procedures, each of the reactants encompassed by formula XVI, above, is prepared.

Preparation 8

Endo-6-(1,2-dihydroxyheptyl)-bicyclo[3.1.0]hexan-3-one (formula XVII: $R_2$ is pentyl, $R_3$ and $R_4$ are hydrogen, ~ is endo)

A solution of potassium chlorate (1.0 g.) and osmium tetroxide (0.065 g.) in 25 ml. of water is added with stirring to a solution of the product (1.0 g.) of Preparation 7. The mixture is stirred vigorously for 5 hours at 50° C. Then, the nearly colorless mixture is concentrated under reduced pressure. The residue is extracted repeatedly with dichloromethane, and the combined extracts are dried and evaporated to give 1.2 g. of a dark oil. This oil is chromatographed on 100 g. of silica gel, and eluted successively with 300 ml. of 10% ethyl acetate in a mixture of isomeric hexanes (Skellysolve B), with 500 ml. of 25% ethyl acetate in Skellysolve B, and then with 50% ethyl acetate in Skellysolve B, collecting 100 ml. eluate fractions. Fractions 13–19 (50% ethyl acetate) were combined and evaporated to dryness to give 867 mg. of endo-6-(1,2-dihydroxyheptyl)-bicyclo[3.1.0]hexan-3-one.

Following the procedure of Preparation 8 but using as reactants the endo and the exo 1-pentenyl, 1-hexenyl, 1-octenyl, and 1-noneyl compounds corresponding to the 1-heptenyl bicyclo[3.1.0]hexane reactant of Preparation 8, the corresponding endo and exo 1,2-dihydroxypentyl, 1,2-dihydroxyhexyl, 1,2-dihydroxyoctyl, and 1,2-dihydroxynonyl bicyclo[3.1.0]hexane products are obtained.

Also following the procedure of Preparation 8 but using as reactants the endo and the exo compounds with X—(CH$_2$)$_d$—CH=CH— in place of the 1-heptenyl moiety of the reactant of Preparation 8, the corresponding X—(CH$_2$)$_d$—CHOH—CHOH—bicyclo[3.1.0]hexane products are obtained.

Also following the procedure of Preparation 8 but as reactants using the endo and the exo compounds with

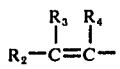

in place of the 1-heptenyl moiety of the reactant of Preparation 8, the corresponding

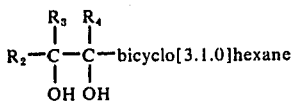

products are obtained.

Preparation 9

1-Tetrahydropyranyloxy-4-bromobutane (Formula XXIII: A is trimethylene)

Concentrated hydrobromic acid (75 drops of 48%) is added with stirring to a mixture of 4-bromobutanol (150 ml.) and dihydropyran (300 ml.) at 0°. This mixture is stirred and allowed to warm slowly to 25° C. during 15 hours. Evaporation under reduced pressure gives a residue which is divided into two equal parts, each part being chromatographed on 1.5 kg. of silica gel, each column being eluted with 7.5 l. of 5% ethyl acetate in Skellysolve B, and then with 4 l. of 7.5% ethyl acetate in Skellysolve B, collecting 500 ml. fractions. Fractions 5–11 from each column are evaporated to give a total of 240 g. of 1-tetrahydropyranyloxy-4-bromobutane.

Preparation 10

7-Tetrahydropyranyloxyhept-2-yne-1-ol (Formula XXII: A is trimethylene)

Lithium metal (7.7 g.) is added in small pieces with stirring to a solution of ferric nitrate (300 mg.) in 1 l. of liquid ammonia. The mixture is then stirred under reflux until the blue color is replaced by a pale grey color. Then, a solution of propargyl alcohol (28 g.) in 250 ml. of diethyl ether is added slowly with stirring. After stirring 2 hours under reflux, a solution of 1-tetrahydropyranyloxy-4-bromobutane (118 g.) in 250 ml. of diethyl ether is added slowly with stirring. After stirring 4 hours under reflux, 300 ml. of water and then 300 ml. of diethyl ether are added. The mixture is stirred about 15 hours, the ammonia being allowed to evaporate during that time. The diethyl ether layer is separated, washed with water and with saturated aqueous sodium chloride solution, dried, and evaporated under reduced pressure to give a residue. The residue is chromatographed on 4 kg. of silica gel, eluting with 8 l. 20%, 6 l. 40%, 6 l. 60%, 6 l. 80%, and 9 l. 100% ethyl acetate-Skellysolve B mixtures, collecting 1.5 l. fractions. Fractions 9–12 are combined and evaporated to give 56 g. of 7-tetrahydropyranyloxyhept-2-yne-1-ol.

Preparation 11

1-Bromo-7-tetrahydropyrayloxyhept-2-yne (Formula XX: A is trimethylene)

Methanesulfonyl chloride (20.3 ml.) is added slowly with stirring to a solution of 7-tetrahydropyranyloxyhept-2-yne-1-ol (52.5 g.) in 400 ml. of pyridine at −20° C. The mixture is stirred one hour at −20° C., and then is poured into a stirred mixture of 3-normal hydrochloric acid (1727 ml.) and 2540 ml. of ice water. This mixture is extracted with diethyl ether. The extract is washed with cold one normal hydrochloric acid and then with saturated aqueous sodiun chloride solution, dried, and evaporated at reduced pressure. The residue is dissolved in 500 ml. of dry acetone. Lithium bromide (26 g.) is added to the acetone solution, and the mixture is stirred and heated at reflux one hour, and then kept at 25° C. for 15 hour. The acetone is evaporated under reduced pressure, and the residue is extracted with diethyl ether. The diethyl ether extract is washed with water and then three times with saturated aqueous sodium chloride solution, dried, and evaporated. The residue is chromatographed on 3.5 kg. of silica gel, eluting with 24 l. of 10% ethyl acetate in Skellysolve B, collecting 1.5 l. fractions. Fractions 5–10 are combined and evaporated to give 25 g. of 1-bromo-7-tetrahydropyranyloxyhept-2-yne.

Following the procedures of Preparations 9, 10, and 11 but using in Preparation 9, omega-bromoalcohols of the formula Br—$(CH_2)_b$—Z—$CH_2OH$ wherein b is zero, one, 2, or 3, and Z is ethylene substituted by one or 2 fluoro, methyl, or ethyl, or by one alkyl of 3 or 4 carbon atoms, in place of 4-bromobutanol, there are obtained compounds corresponding to the product of Preparation 11 with —$(CH_2)_b$-Z in place of trimethylene.

Also following the procedures of Preparations 9, 10, and 11 but using in Preparation 9, omega-bromoalcohols of formula XXIV (Chart C), i.e., Br—A—$CH_2OH$, wherein A is as defined above, in place of 4-bromobutanol, there are obtained compounds corresponding to the product of Preparation 11 with —A— in place of trimethylene.

EXAMPLE 1

Endo-6-(1,2-dihydroxyheptyl)-bicyclo[3.1.0]-hexan-3-one acetonide (Formula XVIII; $R_2$ is pentyl, $R_3$ and $R_4$ are hydrogen, $R_{12}$ and $R_{13}$ are methyl, ~is endo)

A solution of the product (8.42 g.) of Preparation 8 and 700 mg. of potassium bisulfate in 140 ml. of acetone is stirred at 25° C. for 64 hours. Then, sodium carbonate monohydrate (710 mg.) is added, and the mixture is stirred 10 minutes. The acetone is evaporated at reduced pressure, and water is added. The aqueous solution is extracted repeatedly with dichloromethane, and the extracts are combined, washed with water, dried, and evaporated to give 93 g. of an oil. The oil is chromatographed on 400 g. of silica gel, being eluted with 2 l. of 10% ethyl acetate in Skellysolve B, and then with 4 l. of 15% ethyl acetate in Skellysolve B. The 15% ethyl acetate eluates are evaporated to give 7.4 g. of endo-6-(1,2-dihydroxyheptyl)-bicyclo[3.1.0-]hexan-3-one acetonide; infrared absorption at 3000, 1745, 1370, and 1045 $cm^{-1}$; NMR peaks at 4.2–3.8 (multiplet), 3.5 (doublet), 2.9–2.0 (multiplet), 1.25 (singlet), and 0.91 (triplet)δ.

Following the procedure of Example 1 but using as reactants the endo and the exo 1,2-dihydroxypentyl, 1,2-dihydroxyhexyl, 1,2-dihydroxyoctyl, and 1,2-dihydroxynonyl compounds corresponding to the 1,2-dihydroxyheptyl bicyclo[3.2.1]hexane reactant of Example 1, the corresponding acetonides are obtained.

Also following the procedure of Example 1 but using a reactants the endo and exo compounds with x—$(CH_2)_d$—CHOH—CHOH— in place of the 1,2-dihydroxyheptyl moiety of the reactant of Example 1, the corresponding acetonides are obtained.

Also following the procedure of Example 1 but using as reactants the endo and exo compounds with

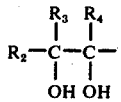

in place of the 1,2-dihydroxyheptyl of the reactant of Example 1, the corresponding acetonides are obtained.

EXAMPLE 2

Endo-6-(1,2-dihydroxyheptyl)-2-(7-hydroxyhept-2-yn-α-yl)-bicyclo[3.1.0]hexan-3-one acetonide (Formula XXV: $R_2$ is pentyl, $R_3$ and $R_4$ are hydrogen, $R_{12}$ and $R_{13}$ are methyl, A is trimethylene, ~is endo and alpha)

A solution of potassium tert-butoxide (3.15 g.) in 100 ml. of dry tetrahydrofuran is added gradually during 2 hours to a solution of endo-6-(1,2-dihydroxyheptyl)-bicyclo[3.1.0]hexan:3-one acetonide (7.0 g.) and 1-bromo-7-tetrahydropyranyloxyhept-2-yne (17.5 g.) in 125 ml. of dry tetrahydrofuran at about 25°C. Water (200 ml.), and then ethyl acetate (200 ml.) are added, and the organic layer is washed with saturated aqueous sodium chloride solution, dried, and evaporated to give endo-6-(1,2-dihydroxyheptyl)-2-(7-tetrahydropyranyloxyhept-2-yn-α-yl)-bicyclo[3.1.0]hexan-3-one acetonide in the form of a yellow oil.

The yellow oil is dissolved in 450 ml. of methanol, and oxalic acid (7.5 g.) is added. This solution is stirred at 25° C. for 4.5 hours. Then, sodium bicarbonate (10 g.) is added, and the mixture is concentrated to a small volume and taken up in ethyl acetate. The ethyl acetate solution is washed with water, dried, and evaporated. The residue is chromatographed on one kg. of magnesium trisilicate (Florisil), eluting with 4 l. each of 5, 10, 15, 20, 25, and 50% acetone in Skellysolve B, collecting 750 ml. fractions. Fractions 11–16 are combined and evaporated to give 3.65 g. of endo-6-(1,2-dihydroxyheptyl)-2-(7-hydroxyhept-2-yn-α-yl)-bicyclo[3.1.0]hexan-3-one acetonide; infrared absorption at 3300 and 1745 $cm^{-1}$.

Following the procedure of Example 2 but using excess potassium tert-butoxide (9 g.) and maintaining the reaction mixture for 8 hours at 25°C. before the addition of water, the product obtained contains substantial amounts of the beta isomer of the Example 2 product, with respect to the —$CH_2$—C≡C—$(CH_2)_3$—$CH_2OH$ chain. This beta isomer is separated from the alpha isomer, which is also present, by silica gel chromatography with mixtures of ethyl acetate and Skellysolve B.

Following the procedure of Example 2 but using as alkylating agents, compounds of the formula

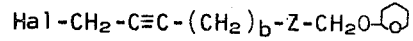

wherein Hal is bromine or iodine, and b and Z are as defined above, in place of the 1-bromo-7-tetrahydropyranyloxyhept-2-yne reactant of Example 2, there are obtained compounds corresponding to the alpha product of Example 2 with —$CH_2$—C≡C—$(CH_2)_b$—Z—$CH_2OH$ in place of —$CH_2$—C≡C—$(CH_2)_3$—$CH_2OH$. As for Example 2, with excess base and a longer reaction time, the products also contain substantial amounts of the corresponding beta isomer which is separated from the alpha isomer a described above.

Also following the procedure of Example 2 but using as alkylating agents, compounds of the formula

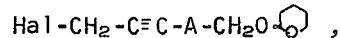, wherein Hal and A are as defined above, there are obtained compounds corresponding to the alpha product of Example 2 with —CH₂—C≡C—A—CH₂OH in place of —CH₂—C≡C—(CH₂)₃—CH₂OH. As for Example 2, with excess base and a longer reaction time, the products also contain substantial amounts of the corresponding beta isomer which is separated from the alpha isomer as described above.

Also following the procedure of Example 2 but using as bicyclo[3.1.0]hexane reactants, endo and exo compounds with 1,2-dihydroxypentyl, 1,2-dihydroxyhexyl, 1,2-dihydroxyoctyl, 1,2-dihydroxynonyl, X—(CH₂-)_d—CHOH—CHOH—, and

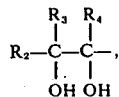

all in acetonide form, wherein d, X, R₂, R₃ and R₄ are as defined above, in place of the 1,2-dihydroxyheptyl acetonide moiety of the Example 2 reactant, there are obtained compounds corresponding to the alpha product of Example 2 with one of those acetonide moieties in place of the 1,2-dihydroxyheptyl acetonide moiety of the Example 2 product. As for Example 2, with excess base and a longer reaction time, the products also contain substantial amounts of the corresponding beta isomer which is separated from the alpha isomer as described above.

Also following the procedure of Example 2 but using in combination, each of the above-defined alternative alkylating agents and each of the above-defined alternative bicyclo [3.1.0]-hexane reactants, there are obtained compounds corresponding to the alpha product of Example 2 but different therefrom with respect to both the acetonide moiety and the acetonide moiety and the acetylenic moiety. As for Example 2, with excess base and a longer reaction time, the products also contain substantial amounts of the corresponding beta isomer which is separated from the alpha isomer as described above

EXAMPLE 3

Endo-6-(1,2-dihydroxyheptyl)-2-(6-carboxyhex-2-yn-α-yl)-bicyclo[3.1.0]hexan-3-one Acetonide (Formula XXVI: R₂ is pentyl, R₃ and R₄ are hydrogen, R₁₂ and R₁₃ are methyl, A is trimethylene, ~ is endo and alpha)

Jones reagent (Preparation 4) is slowly added (10 minutes) to a solution of endo-6-(1,2-dihydroxyheptyl)-2-(7-hydroxyhept-2-yn-α-yl)-bicyclo[3.1.0]hexan-3-one acetonide (3.65 g.) in 500 ml. of acetone at 0°C. until the solution has a permanent pale yellow color. Then, isopropyl alcohol is added until the yellow color changes to green to destroy the excess chromic acid. The reaction mixture is evaporated under reduced pressure, water is added, and the mixture is extracted repeatedly with ethyl acetate. The combined ethyl acetate extracts are washed with water and then with saturated aqueous sodium chloride solution, dried and evaporated to give endo-6-(1,2-dihydroxyheptyl)-2-(6-carboxyhex-2-yn-α-yl)-bicyclo[3.1.0]hexan-3-one acetonide; infrared absorption at 3400–2500, 2250, 1750, 1720, 1380, 1250, 1160, 1050, 880, 850, and 815 cm⁻¹.

Following the procedure of Example 3, the beta isomer of the Example 3 bicyclo[3.1.0]hexane reactant is oxidized to the beta isomer of the Example 3 product.

Also following the procedure of Example 3, each of the endo and exo, alpha and beta compounds defined above after Example 2 is oxidized to a product corresponding to the product of Example 3

EXAMPLE 4

Endo-6-(1,2-dihydroxyheptyl)-2-(6-carboxyhex-2-en-α-yl)-bicyclo[3.1.0]hexan-3-one Acetonide (Formula XXVIII: R₂ is pentyl, R₃ and R₄ are hydrogen, R₁₂ and R₁₃ are methyl, A is trimethylene, ~ is endo and alpha)

A solution of endo-6-(1,2-dihydroxyheptyl)-2-(6-carboxyhex-2-yn-α-yl)-bicyclo[3.1.0]hexane-3-one acetonide (500 mg.) in 10 ml. of pyridine is hydrogenated in the presence of a 5% palladium on barium sulfate catalyst (150 mg.) at 25° and atmospheric pressure. During 318 minutes, 90.6 ml. of hydrogen is absorbed. The mixture is filtered and evaporated to a smaller volume. Ethyl acetate is added, and the remaining pyridine is removed by addition of ice and 3 normal hydrochloric acid. The ethyl acetate layer is washed with one normal hydrochloric acid and then with saturated aqueous sodium chloride solution, dried, and evaporated to give endo-6-(1,2-dihydroxyheptyl)-2-(6-carboxyhex-2-en-α-yl)-bicyclo[3.1.0]hexan-3-one acetonide.

The same ethylenic hydrogenation product obtained as described above from 4.0 g. of the same acetylenic reactant is chromatographed on 250 g. of silica gel which has been previously acid-washed to pH 4 (Silicar CC4, 100–200 mesh, Mallinckrodt Co.). The column is eluted with 3 l. of a 25–75% ethyl acetate-Skellysolve B gradient, collecting 100 ml. fractions. Fractions 2-8 are combined and evaporated to give 1.8 g. of the same endo-6-(1,2-dihydroxyheptyl)-2-(6-carboxyhex-2-en-α-yl)-bicyclo[3.1.0]hexan-3-one acetonide; infrared absorption at 3500–2500, 1745, 1710, and 1020 cm⁻¹; NMR peaks at 5.5 (multiplet), 4.2–3.3, 1.45, 1.25, and 0.9 (triplet)δ.

Following the procedures of Example 4, the beta isomer of the Example 4 acetylenic bicyclo[3.1.0]hexane reactant is hydrogenated to the beta isomer of the Example 4 ethylenic bicyclo[3.1.0]hexane product.

Also following the procedures of Example 4, each of the endo and exo, alpha and beta acetylenic compounds defined above after Example 3 is hydrogenated to an ethylenic acetonide product corresponding to the procedure of Example 4.

EXAMPLE 5

Endo-6-(1,2-dihydroxyheptyl)-2-(6-carboxyhex-2-en-α-yl)-bicyclo[3.1.0]hexan-3-one (Formula XXIX: R₂ is pentyl, R₃ and R₄ are hydrogen, A is trimethylene, ~ is endo and alpha)

Concentrated hydrochloric acid (2.5 ml.) is added to a solution of endo-6-(1,2-dihydroxyheptyl)-2-(6-carboxyhex-2-en-α-yl)-bicyclo[3.1.0]hexan-3-one acetonide (2.0 g.) in a mixture of 55 ml. of tetrahydrofuran and 2.5 ml. of water. The mixture is stirred at 25° C. under nitrogen for 5 hours. The tetrahydrofuran is then evaporated under reduced pressure, and the residue is extracted with ethyl acetate. The extract is washed with saturated aqueous sodium chloride solution, dried, and evaporated to give endo-6-(1,2-dihydroxyheptyl)-2-(6- carboxyhex-2-en-α-yl)-bicyclo[3.1.0]hexan-3-one in the form of a pale yellow oil.

EXAMPLE 6

Endo-6-(1,2-dihydroxyheptyl)-2-(6-carboxyhex-2-en-α-yl)-bicyclo[3.1.0]hexan-3-one (Formula XXIX: $R_2$ is pentyl, $R_3$ and $R_4$ are hydrogen, A is trimethylene, ~ is endo and alpha)

Endo-6-(1,2dihydroxyheptyl)-2-(6-carboxyhex-2-en-α-yl)-bicyclo[3.1.0]hexan-3-one acetonide (2.0 g.) is dissolved in 98% formic acid (9 ml.). The solution is diluted with 6 ml. of water, and the mixture is stirred 2 hours at 25° C., and then extracted repeatedly with ethyl acetate. The combined extracts are washed successively with water, aqueous sodium bicarbonate solution, and saturated aqueous sodium chloride solution, dried, and evaporated. The residue is dissolved in 50 ml. of methanol, 10 ml. of saturated aqueous sodium bicarbonate solution is added, and the mixture is kept 15 hours at 25° C. This mixture is then evaporated under reduced pressure, and the residue is acidified with dilute hydrochloric acid and extracted with ethyl acetate. The extract is washed with water and then with saturated aqueous sodium chloride solution, dried, and evaporated to give endo-6-(1,2-dihydroxyheptyl)-2-(6-carboxyhex-2-en-α-yl)-bicyclo[3.1.0]hexan-3-one.

Following the procedures of Examples 5 or 6, the beta isomer of the Example 5 or 6 ethylenic bicyclo[3.1.0]hexane acetonide reactant is hydrolyzed to the beta isomer of the Example 5 or 6 ethylenic bicyclo[3.1.0]hexane glycol product.

Also following the procedures of Examples 5 or 6, each of the endo and exo, alpha and beta ethylenic acetonide compounds defined above after Example 4 is hydrolyzed to an ethylenic glycol product corresponding to the product of Examples 5 and 6.

EXAMPLE 7

Endo-6-(1,2-dihydroxyheptyl)-2-(6-carboxyhex-2-yn-α-yl)-bicyclo[3.1.0]hexan-3-one (Formula XXVII: $R_2$ is pentyl, $R_3$ and $R_4$ are hydrogen, A is trimethylene, ~ is endo and alpha)

Concentrated hydrochloric acid (1.6 ml.) is added to a solution of endo-6-(1,2-dihydroxyheptyl)-2-(6-carboxyhex-2-yn-α-yl)-bicyclo[3.1.0]hexan-3-one acetonide (1.6 g.) in a mixture of 32 ml. of tetrahydrofuran and 16 ml. of water. The mixture is stirred at 25° C. under nitrogen for 15 hours. The tetrahydrofuran is then evaporated under reduced pressure, and the residue is extracted with ethyl acetate. The extract is washed with saturated aqueous sodium chloride solution, dried, and evaporated to give endo-6-(1,2-dihydroxyheptl)-2-(6-carboxyhex-2-yn-α-yl)-bicyclo[3.1.0]hexan-3-one.

EXAMPLE 8

Endo-6-(1,2-dihydroxyheptyl)-2-(6-carboxyhex-2-yn-α-yl)-bicyclo[3.1.0]hexan-3-one (Formula XXVII: $R_2$ is pentyl, $R_3$ and $R_4$ are hydrogen, A is trimethylene, ~ is endo and alpha)

Following the procedure of Example 6 but using the acetylenic acetonide reactant of Example 7 in place of the ethylenic acetonide reactant of Example 6, endo-6-(1,2-dihydroxyheptyl)-2-(6-carboxyhex-2-yn-α-yl)-bicyclo[3.1.0]hexan-3-one is obtained.

Following the procedures of Examples 7 or 8, the beta isomer of the Example 7 or 8 acetylenic bicyclo[3.1.0]hexane acetonide is hydrolyzed to the beta isomer of the Example 7 or 8 acetylenic bicyclo[3.2.0]hexane glycol product.

Also following the procedures of Examples 7 or 8, each of the endo and exo, alpha and beta acetylenic acetonide compounds defined above after Example 3 is hydrolyzed to an acetylenic glycol product corresponding to the product of Examples 7 and 8.

EXAMPLE 9

Endo-6-(1,2-dihydroxyheptyl)-2-(6-carboxyhex-2-en-α-yl)-bicyclo[3.1.0]hexan-3-one $\beta,\beta,\beta$-trichloroethyl ester (Formula XXX: $R_2$ is pentyl, $R_3$ and $R_4$ are hydrogen, $R_{14}$ is $\beta,\beta,\beta$-trichloroethyl, A is trimethylene, ~ is endo and alpha)

Successively, $\beta,\beta,\beta$-trichloroethanol (24 ml.), pyridine (12 ml.), and dicyclohexylcarbodiimide (3.2 g.) are added to a solution of the endo-6-(1,2-dihydroxyheptyl)-2-(6-carboxyhex-2-en-α-yl)-bicyclo[3.1.0]hexan-3-one obtained from Example 5 in 120 ml. of dichloromethane. This mixture is stirred for 3 hours at 25° C. under nitrogen. Water (50 ml.) is then added, and the mixture is stirred 10 minutes. The dichloromethane is evaporated under reduced pressure, and the residue is extracted repeatedly with ethyl acetate. The combined extracts are washed with ice-cold 3 normal hydrochloric acid, filtering to remove precipitated dicyclohexylurea. Then, the extracts are washed with aqueous sodium bicarbonate solution and then with saturated aqueous sodium chloride solution, dried, and evaporated under reduced pressure. The residue is chromatographed on 400 g. of silica gel, eluting with 8 l. of a 20–100% ethyl acetate-Skellysolve B gradient, collecting 250-ml. fractions. Fractions 4–8 and 18–29 are combined, retreated with hydrochloric acid in tetrahydrofuran as in Example 5, and then with trichloroethanol, pyridine, and dicyclohexylcarbodiimide as above. Chromatography of the residue from this second esterification as described above gives fractions 9–17 which are combined with fractions 9–17 from the first chromatography. These combined fractions are evaporated under reduced pressure to give a residue which is chromatographed on 100 g. of silica gel impregnated with silver nitrate. Elution is with 2 l. of a 20–100% ethyl acetate-Skellysolve B gradient, collecting 50-ml. fractions. Fractions 5–9 are combined and evaporated to give 800 mg. of endo-6-(1,2-dihydroxyheptyl)-2-(6-carboxyhept-2-en-α-yl)-bicyclo[3.1.0]hexan-3-one $\beta,\beta,\beta$-trichloroethyl ester; infrared absorption at 3300, 3400, 1755, 1745, 1220, 1140, 1050, 935, 875, 810, and 720 cm$^{-1}$; NMR peaks at 4.7—5.3, 4.7 (singlet), 4.2—3.2, 0.9 (triplet)δ; mass spectral molecular ion peaks at 464, 466, and 468.

Example 10

Endo-6-(1,2-dihydroxyheptyl)-2-(6-carboxyhex-2-en-α-yl)-bicyclo[3.1.0]hexan-3-one methyl ester (Formula XXX: $R_2$ is pentyl, $R_3$ and $R_4$ are hydrogen, $R_{14}$ is methyl, A is trimethylene, and ~ is endo and alpha)

A solution of 2 equivalents of diazomethane in 100 ml. of anhydrous diethyl ether is added to the endo-6-(1,2-dihydroxy-heptyl)-2-(6-carboxyhex-2-en-α-yl)-bicyclo[3.1.0]hexan-3-one obtained from Example 6. This mixture is stirred at 25° C. for 15 minutes. Then, the solution is evaporated, and the residue is chromatographed on 400 g. of silica gel, eluting with 8 l. of a 20–100% ethyl acetate-Skellysolve B gradient, collecting 250-ml. fractions. Fractions 9–17 are combined and evaporated under reduced pressure. The residue is chromatographed on 100 g. of silica gel impregnated with silver nitrate, eluting with 2 l. of a 20–100% ethyl acetate-Skellysolve B gradient, collecting 50-ml. fractions. Fractions 5–9 are combined and evaporated to give endo-6-(1,2-dihydroxyheptyl)-2-(6-carboxyhex-2-en-α-yl)-bicyclo[3.1.0]hexan-3-one methyl ester.

Following the procedures of Examples 9 and 10, the beta isomer of the Example 9 or 10 ethylenic bicyclo[3.1.0]hexane glycol is esterified to the corresponding $\beta,\beta,\beta$-trichloroethyl and methyl esters.

Also following the procedures of Examples 9 and 10, each of the endo and exo, alpha and beta ethylenic glycols defined above after Example 6 is esterified to $\beta,\beta,\beta$-trichloroethyl and methyl esters corresponding to the esters of Examples 9 and 10.

EXAMPLE 11

Endo-6-(1,2-dihydroxyheptyl)-2-(6-carboxyhex-2-yn-α-yl)-bicyclo[3.1.0]hexan-3-one $\beta,\beta,\beta$-trichloroethyl ester (Formula XXXII: $R_2$ is pentyl, $R_3$ and $R_4$ are hydrogen, $R_{14}$ is $\beta,\beta,\beta$-trichloroethyl, A is trimethylene, ~ is endo and alpha)

Successively, $\beta,\beta,\beta$-trichloroethanol (9.6 ml.), pyridine (4.8 ml.), and dicyclohexylcarbodiimide (1.28 g.) are added to a solution of the endo-6-(1,2-dihydroxyheptyl)-2-(6-carboxyhex-2-yn-α-yl)-bicyclo[3.1.0]hexan-3-one obtained from Example 7 in 48 ml. of dichloromethane. This mixture is stirred for 3 hours at 25° C. under nitrogen. Water (16 ml.) is then added, and the mixture is stirred 10 minutes. The dichloromethane is evaporated under reduced pressure, and the residue is extracted repeatedly with ethyl acetate. The combined extracts are washed with ice-cold one normal hydrochloric acid and then filtered. The filtrate is washed with aqueous sodium bicarbonate solution and then with saturated aqueous sodium chloride solution, dried, and evaporated under reduced pressure. The residue is chromatographed on 150 g. of silica gel, eluting with 5 l. of a 20–100% ethyl acetate-Skellysolve B gradient, collecting 150-ml. fractions. Fractions 5–8 are evaporated under reduced pressure to give 537 mg. of endo-6-(1,2-dihydroxyheptyl)-2-(6-carboxyhex-2-yn-α-yl)-bicyclo[3.1.0]hexan-3-one $\beta,\beta,\beta$-trichloroethyl ester; NMR peaks at 4.8 (singlet), 4.3–4.0 (multiplet), 3.8–3.5 (multiplet), 2.4–2.1 (multiplet), and 0.9 (triplet)δ.

EXAMPLE 12

Endo-6-(1,2-dihydroxyheptyl)-2-(6-carboxyhex-2-yn-α-yl)-bicyclo[3.1.0]hexan-3-one methyl ester (Formula XXXII: $R_2$ is pentyl, $R_3$ and $R_4$ are hydrogen, $R_{14}$ is methyl, A is trimethylene, ~ is endo and alpha)

Following the procedure of Example 10 but using the endo-6-(1,2-dihydroxyheptyl)-2-(6-carboxyhex-2-yn-α-yl)-bicyclo-[3.1.0]hexan-3-one obtained from Example 8 in place of the ethylenic reactant of Example 10, endo-6-(1,2-dihydroxyheptyl)-2-(6-carboxyhex-2-yn-α-yl)-bicyclo[3.1.0]hexan-3-one methyl ester is obtained.

Following the procedures of Examples 11 and 12, the beta isomer of the Example 11 or 12 acetylenic bicyclo[3.1.0] glycol is esterified to the corresponding $\beta,\beta,\beta$-trichloroethyl and methyl esters.

Also following the procedures of Examples 11 and 12, each of the endo and exo, alpha and beta acetylenic glycols defined above after Example 8 is esterified to $\beta,\beta,\beta$-trichloroethyl and methyl esters corresponding to the esters of Examples 11 and 12.

EXAMPLE 13

Racemic PGE$_2$ (S) and racemic 15-epi-PGE$_2$ (R) $\beta,\beta,\beta$-trichloroethyl esters Methanesulfonyl chloride (2.5 ml.) is added dropwise to a solution of endo-6-(1,2-dihydroxyheptyl)-2-(6-carboxyhex-2-en-α-yl)-bicyclo[3.1.0]hexan-3-one $\beta,\beta,\beta$-trichloroethyl ester (800 mg.) in 25 ml. of pyridine at 0° C. under nitrogen. The mixture is stirred 2 hours while slowly warming to 25° C. The solution is again cooled to 0° C., a mixture of ice and water is added (2 volumes), and the mixture is extracted repeatedly with ethyl acetate. The combined extracts are washed successively with cold water, 3 normal hydrochloric acid, and saturated aqueous sodium chloride solution, dried, and evaporated under reduced pressure to give endo-6-(1,2-dimesyloxyheptyl)-2-(6-carboxyhex-2-en-α-yl)-bicyclo[3.1.0]hexan-3-one $\beta,\beta,\beta$-trichloroethyl ester in the form of pale yellow oil.

The dimesylate is dissolved in acetone (72 ml.) and water (36 ml.), and the solution is stirred under nitrogen at 25° C. for 15 hours. The acetone is removed under reduced pressure, and the residue is extracted repeatedly with ethyl acetate. The combined extracts are washed with saturated aqueous sodium chloride solution, dried, and evaporated. The residue is chromatographed on 100 g. of silica gel, eluting with 2 l. of a 50–100% ethyl acetate-Skellysolve B gradient, collecting 50-ml. fractions. Fractions 3-16 are combined and evaporated to give 604 mg. of endo-6-(1-hydroxy-2-mesyloxyheptyl)-2-(6-carboxyhex-2-en-α-yl)-bicyclo[3.1.0]-hexan-3-one $\beta,\beta,\beta$-trichloroethyl ester, which is used in place of part of the starting glycol in the next run. Fractions 17–19 are combined and evaporated to give 96 mg. of racemic 15-epi-PGE$_2$ $\beta,\beta,\beta$-trichloroethyl ester; NMR peaks at 5.75–5.6 (multiplet), 5.55–5.2, 4.75 (singlet), 4.35–3.8 (multiplet), and 0.9 δ; mass spectrum spectral peaks at 464, 466, and 468; $R_f$ 0.37 on TLC with A-IX system. Fractions 33–44 are combined and evaporated to give 100 mg. of racemic PGE$_2$ $\beta,\beta,\beta$-trichloroethyl ester; NMR peaks at 5.65–5.4 (multiplet), 4.75 (singlet), 4.35-3.8 (multiplet), and 0.9δ; mass spectrum spectral peaks at 464, 466, and 468; $R_f$ 0.26 on TLC with A-IX system.

EXAMPLE 14

Racemic PGE$_2$ (S) and racemic 15-epi-PGE$_2$ (R) methyl esters

Following the procedures of Example 13, endo-6-(1,2-dihydroxyheptyl)-2-(6-carboxyhex-2-en-α-yl)-bicyclo[3.1.0]hexan-3-one methyl ester is transformed first to endo-6-(1,2-dimesyloxyheptyl)-2-(6-carboxyhex-2-en-α-yl)-bicyclo[3.1.0]hexan-3-one methyl ester, and then with acetone and water, to a mixture of products which is separated as described in Example 13 to give endo-6-(1-hydroxy-2-mesyloxyheptyl)-2-(6-carboxyhex-2-en-α-yl)-bicyclo[3.1.0]hexan-3-one methyl ester, racemic PGE$_2$ methyl ester, and racemic 15-epi-PGE$_2$ methyl ester.

Following the procedures of Examples 13 and 14, the beta isomer of the Example 13 or 14 ethylenic bicyclo[3.1.0]hexane glycol ester reactant is transformed to first the corresponding intermediate ethylenic bicyclo[3.1.0]hexane dimesylate ester, and then to a mixture of the corresponding ethylenic bicyclo-[3.1.0]hexane monomesylate, racemic 8-iso-PGE$_2$, and racemic 8-iso-15-epi-PGE$_2$ $\beta,\beta,\beta$-trichloroethyl and methyl esters, which are separated as described in Example 13.

Also following the procedures of Examples 13 and 14, each of the endo and exo, alpha and beta ethylenic glycol $\beta,\beta,\beta$-trichloroethyl and methyl esters defined above after Example 10 is transformed first to a dimesylate corresponding to the intermediate ethylenic bicyclo[3.1.0]hexane dimesylate ester products of Examples 13 and 14, and then to the $\beta,\beta,\beta$-trichloroethyl and methyl esters of a monomesylate, a racemic PGE$_2$-type compound, and a racemic 15-epi-PGE$_2$-type compound, each corresponding to one of the three final products of Examples 13 and 14.

EXAMPLE 15

Racemic 5,6-dehydro-PGE$_2$ (S) and racemic 5,6-dehydro-15-epi-PGE$_2$ (R) $\beta,\beta,\beta$-trichloroethyl esters Methanesulfonyl chloride (1 ml.) is added dropwise to a solution of endo-6-(1,2-dihydroxyheptyl)-2-(6-carboxyhex-2-yn-$\alpha$-yl)-bicyclo[3.1.0]hexan-3-one $\beta,\beta,\beta$-trichloroethyl ester (537 mg.) in 10 ml. of pyridine at 0° C. under nitrogen. The mixture is stirred 2 hours while slowly warming to 25° C. The solution is again cooled to 0° C., a mixture of ice and water is added, and the mixture is extracted repeatedly with ethylacetate. The combined extracts are washed successively with cold water, 3 normal hydrochloric acid, and saturated aqueous sodium chloride solution, dried, and evaporated under reduced pressure to give endo-6-(1,2-dimesyloxyheptyl)-2-(6-carboxyhex-2-yn-$\alpha$-yl)-bicyclo[3.1.0]hexan-3-one $\beta,\beta,\beta$-trichloroethyl ester.

The dimesylate is dissolved in acetone (30 ml.) and diluted with water (15 ml.). This solution is stirred under nitrogen at 25° C. for 15 hours. The acetone is removed under reduced pressure, and the residue is extracted repeatedly with ethylacetate. The combined extracts are washed with saturated aqueous sodium chloride solution, dried, and evaporated. The residue is chromatographed on 75 g. of silica gel, eluting with 1.5 l. of a 50–100% ethyl acetate-Skellysolve B gradient, collecting 50-ml. fractions. Early fractions are combined and evaporated to give endo-6-(1-hydroxy-2-mesyloxyheptyl)-2-(6-carboxyhex-2-yn-$\alpha$-yl)-bicyclo[3.1.0]hexan-3-one $\beta,\beta,\beta$-trichloroethyl ester. Fractions 11–15 are combined and evaporated to give 29 mg. of racemic 5,6-dehydro-15-epi-PGE$_2$ $\beta,\beta,\beta$-trichloroethyl ester; NMR peaks at 5.9–5.65, 4.8 (singlet), 4.4–4.0, 2.4–2.1 (multiplet), and 0.9 (triplet)$\delta$. Fractions 18–24 are combined and evaporated to give 28 mg. of racemic 5,6-dehydro-PGE$_2$ $\beta,62$ ,$\beta$-trichloroethyl ester; NMR peaks at 5.8–5.5, 4.8 (singlet), 4.4–4.0, 2.4–2.1 (multiplet), and 0.9 (triplet)$\delta$.

EXAMPLE 16

Racemic 5,6-dehydro-PGE$_2$ (S) and racemic 5,6-dehydro-15-epi-PGE$_2$ (R) methyl esters Following the procedure of Example 15, endo-6-(1,2-dihydroxyheptyl)-2-(6-carboxyhex-2-en-$\alpha$-yl)-bicyclo[3.1.0]hexan-3-one methyl ester is transformed first to the corresponding dimesylate, and then with acetone and water, to a mixture of products which is separated as described in Example 15 to give endo-6-(1-hydroxy-2-mesyloxyheptyl)-2-(6-carboxyhex-2-yn-$\alpha$-yl)-bicyclo[3.1.0]hexan-3-one methyl ester, racemic 5,6-dehydro-PGE$_2$ methyl ester, and racemic 5,6-dehydro-15-epi-PGE$_2$ methyl ester.

Following the procedures of Examples 15 and 16, the beta isomer of the Example 15 or 16 acetylenic bicyclo[3.1.0]hexane glycol ester reactant is transformed first to the corresponding intermediate dimesylate, and then to the corresponding monomesylate, racemic 5,6-dehydro-8-iso-PGE$_2$, and racemic 5,6-dehydro-8-iso-15-epi-PGE$_2$ $\beta,\beta,\beta$-trichloroethyl and methyl esters, which are separated as described in Example 15.

Also following the procedures of Examples 15 and 16, each of the endo and exo, alpha and beta acetylenic glycol $\beta,\beta,\beta$-trichloroethyl and methyl esters defined above after Example 12 is transformed first to a dimesylate corresponding to the intermediate dimesylate products of Examples 15 and 16, and then to the $\beta,\beta,\beta$-trichloroethyl and methyl esters of a monomexylate, a racemic 5,6-dehydro-PGE$_2$-type ester, and a racemic 5,6-dehydro-15-epi-PGE$_2$-type ester, each corresponding to one of the three final products of Examples 15 and 16.

EXAMPLE 17

Racemic PGE$_2$ (S)

Zinc dust (400 mg.) is added to a solution containing racemic PGE$_2$ $\beta,\beta,\beta$-trichloroethyl ester (100 mg.) in 5 ml. of a mixture of acetic acid and water (9:1 v/v). This mixture is stirred under nitrogen 2 hours at 25° C. Ethyl acetate (4 volumes) is then added, followed by addition of one normal hydrochloric acid (one volume). The ethyl acetate layer is separated, washed with water and then with saturated aqueous sodium chloride solution, dried, and evaporated. The residue is chromatographed on 15 g. of acid-washed silica gel (Silicar CC4), being eluted with 100 ml. of 50%, 100 ml. of 80%, and 200 ml. of 100% ethyl acetate in Skellysolve B, collecting 20-ml. fractions. Fractions 13–18 are combined and evaporated to give racemic PGE$_2$; same mobility as optically active PGE$_2$ and same color (with vanillin-phosphoric acid spray) on TLC silica gel and silver nitrate-impregnated silica gel plates; NMR peaks and infrared absorption (CH$_2$Cl$_2$ solution) same as optically active PGE$_2$; mass spectrum spectral peaks at 316, 298, 279, and 190.

EXAMPLE 18

Racemic 15-epi-PGE$_2$ (R)

Following the procedure of Example 17, racemic 15-epi-PGE$_2$ $\beta, \beta, \beta$-trichloroethyl ester is transformed to 15-epi-PGE$_2$; NMR peaks at 5.8–5.6 (multiplet), 5.6–5.3 (multiplet), 4.5–3.9 (multiplet), and 0.9 (triplet) $\delta$.

EXAMPLE 19

Racemic 5,6-dehydro-PGE$_2$ (S)

Zinc dust (150 mg.) is added to a solution containing racemic 5,6-dehydro-PGE$_2$ (28 mg.) in 1.5 ml. of a mixture of acetic acid and water (9:1 v/v). This mixture is stirred under nitrogen for 2 hours at 25° C. Ethyl acetate (4 volumes) is then added. The ethyl acetate layer is washed with one normal hydrochloric acid and then with saturated aqueous sodium chloride solution, dried, and evaporated. Benzene is added to the residue and then evaporated under reduced pressure. The residue is chromatographed on 5 g. of acid-washed silica gel (Silicar CC4), eluting with 100 ml. of 75% ethyl acetate in Skellysolve B, and then with 100 ml. ethyl acetate, collecting 10 ml. fractions. Fractions 8–11 are combined and evaporated to give 21 mg. of crystalline racemic 5,6-dehydro-$PGE_2$; m.p. 85°–90° C.; recrystallized twice from a mixture of ethyl acetate and Skellysolve B, m.p. 89°–91° C.; mass spectrum spectral peaks at 332, 314, 296, 261, and 243.

EXAMPLE 20

Racemic 5,6-dehydro-15-epi-$PGE_2$ (R)

Following the procedure of Example 19, racemic 5,6-dehydro-15-epi-$PGE_2$ $\beta,\beta,\beta$-trichloroethyl ester is transformed to 5,6-dehydro-15-epi-$PGE_2$.

Following the procedures of Examples 17 and 19, the beta isomers of the $\beta,\beta,\beta$-trichloroethyl esters of racemic $PGE_2$, racemic 15-epi-$PGE_2$, racemic 5,6-dehydro-$PGE_2$, and racemic 5,6-dehydro-15-epi-$PGE_2$ are each transformed to racemic 8-iso-$PGE_2$, racemic 8-iso-15-epi-$PGE_2$, racemic 5,6-dehydro-8-iso-$PGE_2$, and racemic 5,6-dehydro-8-iso-15-epi-$PGE_2$, respectively.

Also following the procedure of Example 17, each of $\beta,\beta,\beta$-trichloroethyl esters of the racemic $PGE_2$-type compounds and the racemic 15-epi-$PGE_2$-type compounds defined above after Example 14 is transformed to the corresponding racemic $PGE_2$-type acid and the racemic 15-epi-$PGE_2$-type acid, including the corresponding 8-iso acids.

Also following the procedure of Example 19, each of the $\beta,\beta,\beta$-trichloroethyl esters of the racemic 5,6-dehydro-$PGE_2$-type compounds and the racemic 5,6-dehydro-15-epi-$PGE_2$-type compounds defined above after Example 16 is transformed to the corresponding racemic 5,6-dehydro-$PGE_2$-type acid and the racemic 5,6-dehydro-15-epi-$PGE_2$-type acid, including the 8-iso acids.

EXAMPLE 21

Racemic $PGE_2$

A. Enzyme preparation

A medium is prepared consisting of 2% corn steep liquor (a mixture of equal parts of cerelose and glucose) in tap water. This is brought to pH 4.5 by adding hydrochloric acid, and 1% of methyl oleate is added. Four 500 ml. flasks each containing 100 ml. of the above medium are inoculated with Cladosporum resinae (C1-11, ATCC 11,274) and are placed on a shaker at room temperature (about 28° C.) for 4 days. The culture is then placed in 40 ml. centrifuge tubes and centrifuged at about 2000 rmp. in a clinical centrifuge. The liquid is decanted from the centrifuge tubes and the collected cells are washed with cold water. The washed cells from 2centrifuge tubes are suspended in 50 ml. of ice cold 0.05 M pH 7.0 phosphate buffer and placed in small Waring blender cup chilled with ice. Glass beads are added and the suspended cells are churned in the blender for 15 minutes. The resulting suspension of broken cells is centrifuged in a clinical centrifuge at about 2000 r.p.m. for 15 minutes at room temperature, then the supernatant liquid is collected. This supernatant liquid contains Cladosporium resinae acylase and is used directly for the hydrolysis of $PG_2$-type alkyl esters or is stored, preferably frozen, until needed.

B. Esterase hydrolysis of racemic $PGE_2$ methyl ester

Ten milliliters of the supernatant liquid containing Cladosporium resinae acylase, prepared as described in part A of this example and 50 mg. of racemic $PGE_2$ methyl ester are shaken at room temperature under nitrogen for about 19 hrs., then 70 ml. of acetone is added and the mixture is filtered giving a filtrate and an insoluble residue. The filtrate is evaporated under reduced pressure and gives 40–50 mg. of a slightly yellow oil comprising racemic $PGE_2$. Both this oil and the insoluble residue are combined and chromatographed over 10 g. of acid washed silica gel (Silic ARCC-4, Mallinckrodt). Elution is with mixed hexanes (Skellysolve B) containing increasing amounts of ethyl acetate, collecting 50 ml. fractions as follows:

| Fraction | Solvent |
| --- | --- |
| 1 | Skellysolve B |
| 2 | 40 ml. Skellysolve B - 10 ml. ethyl acetate |
| 3 | 30 ml. Skellysolve B - 20 ml. ethyl acetate |
| 4 | 25 ml. Skellysolve B - 25 ml. ethyl acetate |
| 5 | 20 ml. Skellysolve B - 30 ml. ethyl acetate |
| 6 | 10 ml. Skellysolve B - 40 ml. ethyl acetate |
| 7 | 5 ml. Skellysolve B - 45 ml. ethyl acetate |
| 8 | ethyl acetate |
| 9 | ethyl acetate |
| 10 | ethyl acetate |
| 11 | ethyl acetate |
| 12 | 100 ml. of ethyl acetate |

Fractions 6 to 12 are combined and evaporated to give racemic $PGE_2$ with substantially the same properties as that obtained according to Example 17.

Following the procedure of Example 21, each of the methyl esters of the $PGE_2$-type and 5,6-dehydro-$PGE_2$-type compounds defined above after Examples 14 and 16 are enzymatically hydrolyzed to the corresponding free acid.

Also following the procedure of Example 21, each of the methyl esters of the $PGF_2$-type, $PGA_2$-type, $PGB_2$-type and the corresponding 5,6-dehydro-$PG_2$-type compounds defined hereinafter is enzymatically hydrolyzed to the corresponding free acid.

EXAMPLE 22

Racemic $PGF_{2\alpha}$ and racemic $PGF_2\beta$.

A solution of sodium borohydride (70 mg.) in 5 ml. of ice-cold methanol is added dropwise with stirring to a solution of racemic $PGE_2$ (22 mg.) in 1.5 ml. of methanol at 0°C. This mixture is stirred at 0° C. for 30 minutes, and is then stirred and allowed to warm to 25° C. during one hour. After evaporation, water (10 ml.) is added, and the mixture is acidified with one normal hydrochloric acid, saturated with sodium chloride, and extracted repeatedly with ethyl acetate. The combined extracts are washed with saturated aqueous sodium chloride solution, dried, and evaporated. The residue is chromatographed on 3 g. of acid-washed silica gel (Silicar CC4), eluting with 50 ml. of ethyl acetate and then with 50 ml. of one % methanol in ethyl acetate, collecting 10 ml. fractions. Fractions 4 and 5 are combined and evaporated to give 11 mg. of racemic $PGF_{2\alpha}$; same mobility as optically active $PGF_{2\alpha}$ on TLC silica gel and silver-nitrate impregnated silica gel plates with the A IX system twice; mass spectrum spectral peaks same as for optically active $PGF_{2\alpha}$. Fractions 7–9 are combined and evaporated to give 14 mg. of racemic PGF$_2\beta$; m.p. 85°–92° C.; recrystallized twice from ethyl acetate, m.p. 92°–93° C.; same mobility as optically active PGF$_2\beta$ on TLC silica gel plates as for PGF$_2\beta$; mass spectrum spectral peaks same as for optically active PGF$_2\beta$.

EXAMPLE 23

Racemic 15-epi-PGF$_{2\alpha}$ and racemic 15-epi-PGF$_2\beta$

Following the procedure of Example 22, 20 mg. of racemic 15-epi-PGE$_2$ is reduced with sodium borohydride to give racemic 15-epi-PGF$_{2\alpha}$ and racemic 15-epi-PGF$_2\beta$, separated by chromatography on Silicar CC4, eluting successively with 50, 75, and 100% ethyl acetate in Skellysolve B.

Following the procedure of Example 22, racemic 8-iso-PGE$_2$ and racemic 8-iso-15-epi-PGE$_2$ are each reduced to the alpha and beta isomers of racemic 8-iso-PGE$_2$ and racemic 8-iso-15-epi-PGF$_2$, respectively, the alpha and beta pairs being separated in each as described in Examples 22 or 23.

Also following the procedure of Example 22, each of the racemic PGE$_2$-type compounds, 5,6-dehydro-PGE$_2$, 5,6-dehydro-15-epi-PGE$_2$, 5,6-dehydro-8-iso-PGE$_2$, 5,6-dehydro-8-iso-15-epi-PGE$_2$, and each of the other 5,6-dehydro-PGE$_2$-type compounds defined above is reduced to the alpha and beta isomers of the corresponding PGF$_2$-type and 5,6-dehydro-PGF$_2$-type compound. In each case, the alpha and beta isomers are separated as described in Examples 22 or 23.

EXAMPLE 24

Racemic PGA$_2$ (S) and racemic 15-epi-PGA$_2$ (R)

Endo-6-(1,2-dimesyloxyheptyl)-2-(6-carboxyhex-2-en-$\alpha$-yl)-bicyclo[3.1.0]hexan-3-one $\beta,\beta,\beta$-trichloroethyl ester is prepared as described in Example 13 from 800 mg. of glycol.

The dimesylate is dissolved in 75 ml. of acetone to which is added 10 ml. of water and 20 ml. of saturated sodium bicarbonate solution. This mixture is refluxed under nitrogen for 4 hours. After acidification with one normal hydrochloric acid, the mixture is extracted with ethyl acetate, and the extracts are washed, dried, and evaporated to give the $\beta,\beta,\beta$-trichloroethyl ester of racemic PGA$_2$. That ester is transformed to racemic PGA$_2$ by the procedure of Example 17, the racemic PGA$_2$ being purified by the procedure of Pike et al., above cited.

Following the procedure of Example 24 and using each of the above defined exo and endo, alpha and beta, ethylenic and acetylenic bicyclo[3.1.0]hexane glycol $\beta,\beta,\beta$-trichloroethyl esters following Examples 9, 10, 11, and 12, there are obtained each of the corresponding racemic PGA$_2$-type and 5,6-dehydro-PGA$_2$-type compounds including 15-epi-PGA$_2$, 8-iso-PGA$_2$, 8-iso-15-epi-PGA$_2$, 5,6-dehydro-PGA$_2$, 5,6-dehydro-15-epi-PGA$_2$, 5,6-dehydro-8-iso-PGA$_2$, and 5,6-dehydro-8-iso-15-epi-PGA$_2$.

Each of the above-defined racemic PGA$_2$-type compounds and 5,6-dehydro-PGA$_2$-type compounds is also prepared from the corresponding PGE$_2$-type and 5,6-dehydro-PGA$_2$-type compound by acetic acid dehydration as described by Pike et al., above cited, and in British Pat. Specification No. 1,097,533.

EXAMPLE 25

Racemic PGB$_2$

A solution of racemic PGE$_2$ (200 mg.) in 100 ml. of 50% aqueous ethanol containing 10 grams of potassium hydroxide is kept at 25° C. for 10 hours under nitrogen. Then, the solution is cooled to 10° C. and neutralized by addition of 3 normal hydrochloric acid at 10° C. The resulting solution is extracted repeatedly with ethyl acetate, and the combined ethyl acetate extracts are washed with water and then with saturated aqueous sodium chloride solution, dried, and evaporated to give racemic PGB$_2$.

Following the procedure of Example 25, racemic PGA$_2$ is transformed to racemic PGB$_2$.

Also following the procedure of Example 25, each of the above defined PGE$_2$-type compounds and each of the above-defined PGA$_2$-type compounds is transformed to the corresponding PGB$_2$-type compound, including 15-epi-PGB$_2$, 5,6-dehydro-PGB$_2$, and 5,6-dehydro-15-epi-PGB$_2$.

EXAMPLE 26

Racemic 8-iso-PGE$_2$ from racemic PGE$_2$

A solution of 1.00 g. of racemic PGE$_2$ and 5 g. of potassium acetate in 100 ml. of 95% ethanol is allowed to stand at room temperature under nitrogen for 6 days; then is concentrated by evaporation under reduced pressure to about one third volume. The concentrated mixture is diluted with 75 ml. of cold water and dilute hydrochloric acid is added until the mixture reaches pH 3. The acidified mixture is extracted twice with ethyl acetate, then is saturated with sodium chloride and extracted once more with ethyl acetate. The ethyl acetate extracts are combined, washed with saturated aqueous sodium chloride, dried over sodium sulfate, and evaporated under reduced pressure, then dried under a stream of nitrogen to remove acetic acid from the residue. Thin layer chromatographic analysis shows that the residue comprises a mixture of racemic PGE$_2$ and racemic 8-iso PGE$_2$. The residue is chromatographed on 200 g. of Silicar CC4, eluting with 500 ml. 40%, 500 ml. 50%, 250 ml. 60%, and 250 ml. 100% ethyl acetate in cyclohexane, collecting 50-ml. fractions. Fractions 23–25 are combined and evaporated to give racemic 8-iso-PGE$_2$. Fractions 27–30 are combined to give racemic PGE$_2$.

EXAMPLE 27

Racemic PGE$_2$ from racemic 8-iso-PGE$_2$

The procedure of Example 26 is followed, using as a starting material racemic 8-iso-PGE$_2$ rather than racemic PGE$_2$. Substantially the same product mixture is obtained.

Following the procedures of Examples 26 or 27, each of the PGE$_2$-type, 8-iso-PGE$_2$-type, 5,6-dehydro-PGE$_2$-type, and 5,6-dehydro-8-iso-PGE$_2$-type compounds defined above is transformed to a mixture of alpha and beta isomers, the two isomers then being separated as described in Example 26.

EXAMPLE 28

Endo-6-(1,2-dihydroxyheptyl)-2-(7-hydroxyhept-2-yn-$\beta$-yl)-bicyclo[3.1.0]hexan-3-one Endo-6-(1,2-dihydroxyheptyl)-2-(7-hydroxyhept-2-yn-$\alpha$-yl)-bicyclo[3.1.0]hexan-3-one (1.2 g.) is dissolved in 100 ml. of dry dimethoxyethane. Potassium tert-butoxide (400mg.) is added, and the mixture is maintained under nitrogen at 25° C. for one hour. Then, sufficient hydrochloric acid (3 N) is added to neutralize the potassium tert-butoxide. The mixture is diluted with 500 ml. of water and then extracted 3 times with 100-ml. portions of ethyl acetate. The ethyl acetate extracts are dried and evaporated to give a residue which is chromatographed over silica gel (elution with 5% ethyl acetate in Skellysolve B) to give after evaporation of the eluates, 380 mg. of starting material (alpha) and 700 mg. of the corresponding beta isomer.

Following the above procedure but using the beta isomer as starting material, the same results are obtained.

I claim:
1. A racemic compound of the combination of the formula:

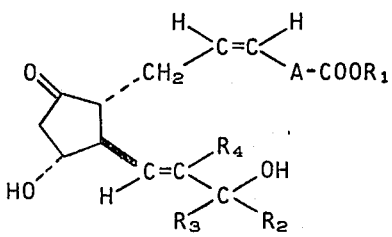

wherein the side-chain hydroxy is in S configuration, and the mirror image of that formula; wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, or phenyl substituted with one to 3 chloro or alkyl of one to 4 carbon atoms, inclusive; wherein $R_2$ is $-(CH_2)_a-CH_3$ wherein $a$ is 2, 3, 4, 5, or 6, or $-(CH_2)_d-X$ wherein $d$ is zero, one, 2, 3, or 4 and X is isobutyl, tert-butyl, 3,3-difluorobutyl, 4,4-difluorobutyl, or 4,4,4-trifluorobutyl; wherein $R_3$ and $R_4$ are hydrogen or alkyl of one to 4 carbon atoms, inclusive; wherein A is $-CH_2-Z-$ wherein Z is ethylene substituted with one or 2 fluoro; and pharmacologically acceptable salts thereof when $R_1$ is hydrogen.

2. A racemic compound according to claim 1 wherein $R_1$ is hydrogen, alkyl of one to 4 carbon atoms, inclusive, or a pharmacologically acceptable cation.

3. A racemic compound according to claim 2 wherein $R_2$ is $-(CH_2)_a-CH_3$ wherein $a$ is 2, 3, 4, 5, or 6.

4. A racemic compound according to claim 2 wherein $R_2$ is pentyl.

5. A racemic compound according to claim 3 wherein Z is ethylene substituted with 2 fluoro on the carbon adjacent to the carboxylate moiety.

6. A racemic compound according to claim 4 wherein Z is ethylene substituted with 2 fluoro on the carbon adjacent to the carboxylate moiety.

7. A racemic compound according to claim 3 wherein $R_3$ and $R_4$ are hydrogen.

8. A racemic compound according to claim 4 wherein $R_3$ and $R_4$ are hydrogen.

9. A racemic compound according to claim 5 wherein $R_3$ and $R_4$ are hydrogen.

10. A racemic compound according to claim 6 wherein $R_3$ and $R_4$ are hydrogen.

11. A racemic compound of the combination of the formula:

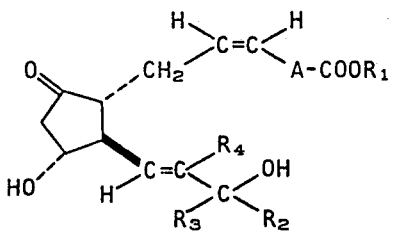

wherein the side-chain hydroxy is in S configuration, and the mirror image of that formula; wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, or phenyl substituted with one to 3 chloro or alkyl of one to 4 carbon atoms, inclusive; wherein $R_2$ is $-(CH_2)_d-X$ wherein $d$ is zero, one, 2, 3, or 4 and X is 3,3-difluorobutyl, 4,4-difluorobutyl, or 4,4,4-trifluorobutyl; wherein $R_3$ and $R_4$ are hydrogen or alkyl of one to 4 carbon atoms, inclusive; wherein A is trimethylene or $-CH_2-Z-$ wherein Z is ethylene substituted with one or 2 fluoro, methyl, or ethyl; and pharmacologically acceptable salts thereof when $R_1$ is hydrogen.

12. A racemic compound according to claim 11 wherein $R_1$ is hydrogen, alkyl of one to 4 carbon atoms, inclusive, or a pharmacologically acceptable cation.

13. A racemic compound according to claim 12 wherein $d$ is one.

14. A racemic compound according to claim 13 wherein A is trimethylene.

15. A racemic compound according to claim 13 wherein A is $-CH_2-Z-$ wherein Z is ethylene substituted with 2 fluoro on the carbon adjacent to the carboxylate moiety.

16. A racemic compound according to claim 14 wherein $R_3$ and $R_4$ are hydrogen.

17. A racemic compound according to claim 15 wherein $R_3$ and $R_4$ are hydrogen.

* * * * * ed Page 1 of 2 Pages

UNITED STATES PATENT OFFICE
CERTIFICATE OF CORRECTION

Patent No. 3,983,153                    Dated September 28, 1976

Inventor(s) William P. Schneider

It is certified that error appears in the above-identified patent and that said Letters Patent are hereby corrected as shown below:

Column 1, line 25: "$PGF_2$" should read: -- $PGF_2\beta$ --.
Column 2, line 45: "$PGF_2\alpha$, $PGB_2\beta$, $PGA_2$," should read: -- $PGF_2\alpha$, $PGF_2\beta$, $PGA_2$, --.
Column 6, lines 6-7: "$-CH_2-CH=\lambda CH-A-COOR_1$" should read: -- $-CH_2-CH=CH-A-COOR_1$ --.
Column 29, line 3-4: "or $Br-CH_2CH_2-Z-CH_2OH$." should read: -- or $Br-CH_2CH_2CH_2-Z-CH_2OH$. --.
Column 29, line 41: "(Chart E) depending" should read: -- (Chart F) depending --.
Column 30, lines 61-62: "$-CH_2-CH=\lambda CH-A-COOR_{14}$" should read: -- $-CH_2-CH=CH-A-COOR_{14}$ --.
Column 34, line 9: "over intermediates for this" should read: -- over the other intermediates for this --.
Column 41, line 28: "(8.42 g.)" should read: -- (8.41 g.) --.
Column 42, line 61: "isomer a described above." should read: -- isomer as described above. --.
Column 43, lines 38-39: "the acetonide moiety and the acetonide moiety." should read: -- the acetonide moiety and the acetylenic moiety. --.
Column 44, line 52: "procedure of Example 4." should read: -- product of Example 4. --.
Column 46, lines 4-5: "bicyclo[3.2.0]hexane" should read: -- bicyclo[3.1.0]hexane --.

UNITED STATES PATENT OFFICE
CERTIFICATE OF CORRECTION

Patent No. 3,983,153  Dated September 28, 1976

Inventor(s) William P. Schneider

It is certified that error appears in the above-identified patent and that said Letters Patent are hereby corrected as shown below:

Column 49, line 59: "β,62,β-trichloroethyl ester;" should read: --β,β,β-trichloroethyl ester; --.

Signed and Sealed this

Seventh Day of February 1978

[SEAL]

Attest:

RUTH C. MASON  
Attesting Officer

LUTRELLE F. PARKER  
Acting Commissioner of Patents and Trademarks